(12) United States Patent
Amirouche

(10) Patent No.: US 10,245,420 B2
(45) Date of Patent: Apr. 2, 2019

(54) MEDICAMENT DISTRIBUTION SYSTEMS AND RELATED METHODS OF USE

(71) Applicant: PicoLife Technologies, Deerfield, IL (US)

(72) Inventor: Farid Amirouche, Highland Park, IL (US)

(73) Assignee: PicoLife Technologies, Highland Park, IL (US)

( * ) Notice: Subject to any disclaimer, the term of this patent is extended or adjusted under 35 U.S.C. 154(b) by 0 days.

(21) Appl. No.: 13/649,202

(22) Filed: Oct. 11, 2012

(65) Prior Publication Data
US 2013/0345650 A1    Dec. 26, 2013

Related U.S. Application Data

(60) Provisional application No. 61/664,516, filed on Jun. 26, 2012.

(51) Int. Cl.
*A61F 13/00*        (2006.01)
*A61M 35/00*       (2006.01)
(Continued)

(52) U.S. Cl.
CPC ......... *A61M 35/00* (2013.01); *A61B 5/04001* (2013.01); *A61B 5/4041* (2013.01);
(Continued)

(58) Field of Classification Search
CPC .. A61M 35/00; A61M 31/002; A61M 35/006; A61M 37/00; A61M 5/14248;
(Continued)

(56) References Cited

U.S. PATENT DOCUMENTS

| 2,398,435 A | 4/1946 | Marks |
| 3,137,242 A | 6/1964 | Hahn |

(Continued)

FOREIGN PATENT DOCUMENTS

| EP | 0 024 431 B1 | 8/1985 |
| EP | 0 299 628 A1 | 1/1989 |

(Continued)

OTHER PUBLICATIONS

R. Barbano et al., "Effectiveness, Tolerability, and Impact on Quality of Life of the 5% Lidocaine Patch in Diabetic Polyneuropathy," Archives of Neurology, vol. 61, No. 6, pp. 914-918, 2004.

(Continued)

*Primary Examiner* — Andrew J Mensh
(74) *Attorney, Agent, or Firm* — Ashkan Najafi

(57) ABSTRACT

Embodiments of the disclosure may include a medical device for releasing a medicament. The device may include a multi-layer patch. The patch may include a base layer configured to secure the patch to a body of a user and a medicament array located adjacent the base layer. The array may include a plurality of wells configured to release a quantity of medicament from the array to the body of the user. The device may also include a cover layer located on a side of the medicament array opposite the base layer and a pump operably coupled to the patch and configured to deliver a quantity of fluid to the patch.

17 Claims, 12 Drawing Sheets

(51) Int. Cl.

| | | |
|---|---|---|
| *A61B 5/04* | (2006.01) | |
| *A61F 13/15* | (2006.01) | |
| *A61F 13/20* | (2006.01) | |
| *A61K 9/70* | (2006.01) | |
| *A61M 37/00* | (2006.01) | |
| *A61M 31/00* | (2006.01) | |
| *A61F 13/40* | (2006.01) | |
| *A61M 5/142* | (2006.01) | |
| *A61B 5/00* | (2006.01) | |
| *A61F 13/84* | (2006.01) | |

(52) U.S. Cl.
 CPC ...... *A61B 5/4839* (2013.01); *A61F 13/00063* (2013.01); *A61B 5/6828* (2013.01); *A61B 2560/0431* (2013.01); *A61F 2013/0017* (2013.01); *A61F 2013/0094* (2013.01); *A61F 2013/00153* (2013.01); *A61F 2013/00272* (2013.01); *A61F 2013/00387* (2013.01); *A61F 2013/00429* (2013.01); *A61F 2013/00646* (2013.01); *A61F 2013/00906* (2013.01); *A61F 2013/8494* (2013.01); *A61H 2201/105* (2013.01); *A61K 9/703* (2013.01); *A61K 9/7084* (2013.01); *A61K 9/7092* (2013.01); *A61M 5/14248* (2013.01); *A61M 31/002* (2013.01); *A61M 35/006* (2013.01); *A61M 37/00* (2013.01)

(58) Field of Classification Search
 CPC .... A61K 9/703; A61K 9/7084; A61K 9/7092; A61H 2201/105; A61F 13/00063; A61F 2013/00153; A61F 2013/0017; A61F 2013/00272; A61F 2013/00387; A61F 2013/00429; A61F 2013/00646; A61F 2013/00906; A61F 2013/0094; A61F 2013/8494; A61B 5/04001; A61B 5/4041; A61B 5/4839; A61B 5/6828; A61B 2560/0431
 USPC ..... 604/289, 304, 307, 369, 378, 890.1, 305
 See application file for complete search history.

(56) References Cited

U.S. PATENT DOCUMENTS

| | | |
|---|---|---|
| 3,498,228 A | 3/1970 | Blumle et al. |
| 3,691,263 A | 9/1972 | Stoy et al. |
| 3,771,694 A | 11/1973 | Kaminski |
| 3,827,565 A | 8/1974 | Matsumura |
| 3,889,710 A | 6/1975 | Brost |
| 3,915,609 A | 10/1975 | Robinson |
| 4,017,238 A | 4/1977 | Robinson |
| 4,197,266 A | 4/1980 | Clark et al. |
| 4,257,416 A | 3/1981 | Prager |
| 4,340,048 A | 7/1982 | Eckenhoff |
| 4,376,618 A | 3/1983 | Toyoda et al. |
| 4,415,003 A | 11/1983 | Paradis et al. |
| 4,498,843 A | 2/1985 | Schneider et al. |
| 4,544,369 A | 10/1985 | Skakoon et al. |
| 4,552,561 A | 11/1985 | Eckenhoff et al. |
| 4,657,486 A | 4/1987 | Stempfle et al. |
| 4,712,583 A | 12/1987 | Pelmulder et al. |
| 4,731,726 A | 3/1988 | Allen, III |
| 4,784,644 A | 11/1988 | Sawyer et al. |
| 4,797,144 A | 1/1989 | DeMeritt et al. |
| 4,840,754 A | 6/1989 | Brown et al. |
| 4,936,833 A | 6/1990 | Sams |
| 4,938,742 A | 7/1990 | Smits |
| 4,946,448 A | 8/1990 | Richmond |
| 4,947,856 A | 8/1990 | Beard |
| 4,958,661 A | 9/1990 | Holtermann et al. |
| 4,966,199 A | 10/1990 | Ruschke |
| 5,019,974 A | 5/1991 | Beckers |
| 5,050,612 A | 9/1991 | Matsumura |
| 5,147,323 A | 9/1992 | Haber et al. |
| 5,218,993 A | 6/1993 | Steinberg et al. |
| 5,246,634 A | 9/1993 | Ichikawa et al. |
| 5,370,635 A * | 12/1994 | Strausak et al. ............. 604/248 |
| 5,584,815 A | 12/1996 | Pawelka et al. |
| 5,645,855 A * | 7/1997 | Lorenz .................... 424/449 |
| 5,674,557 A | 10/1997 | Wildman et al. |
| 5,709,662 A | 1/1998 | Olive et al. |
| 5,762,632 A | 6/1998 | Whisson |
| 5,775,671 A | 7/1998 | Cote, Sr. |
| 5,822,715 A | 10/1998 | Worthington et al. |
| 5,858,001 A | 1/1999 | Tsals et al. |
| 6,003,736 A | 12/1999 | Ljunggren |
| 6,017,331 A | 1/2000 | Watts et al. |
| 6,056,718 A | 5/2000 | Funderburk et al. |
| 6,305,661 B1 | 10/2001 | Kennedy |
| 6,311,712 B1 | 11/2001 | Meyer |
| 6,315,929 B1 | 11/2001 | Ishihara et al. |
| 6,390,120 B1 | 5/2002 | Guala |
| 6,409,707 B1 | 6/2002 | Guala |
| 6,572,586 B1 | 6/2003 | Wojcik |
| 6,627,124 B1 | 9/2003 | Herbrechtsmeier et al. |
| 6,648,859 B2 | 11/2003 | Bitdinger et al. |
| 6,723,086 B2 * | 4/2004 | Bassuk et al. ............. 604/890.1 |
| 6,813,906 B1 | 11/2004 | Hirota et al. |
| 6,945,963 B2 | 9/2005 | Langley et al. |
| 7,044,125 B2 | 5/2006 | Vedrine et al. |
| 7,081,108 B2 | 7/2006 | Langley et al. |
| 7,104,973 B2 | 9/2006 | Woolston et al. |
| 7,123,985 B2 | 10/2006 | Wildsmith et al. |
| 7,296,782 B2 | 11/2007 | Enerson et al. |
| 7,302,311 B2 | 11/2007 | Varis |
| 7,407,490 B2 | 8/2008 | Bendsen et al. |
| 7,470,266 B2 * | 12/2008 | Massengale et al. ...... 604/890.1 |
| 7,510,544 B2 | 3/2009 | Vilks et al. |
| 7,537,590 B2 | 5/2009 | Santini, Jr. et al. |
| 7,585,167 B2 | 9/2009 | Lawton et al. |
| 7,637,899 B2 | 12/2009 | Woolston et al. |
| 7,846,146 B2 | 12/2010 | Woolston et al. |
| 7,850,663 B2 | 12/2010 | Sullivan et al. |
| 7,896,002 B2 | 3/2011 | Watanabe |
| 7,914,499 B2 | 3/2011 | Gonnelli et al. |
| 7,935,280 B2 | 5/2011 | Lawton et al. |
| 7,967,795 B1 | 6/2011 | Cabiri |
| 8,021,334 B2 | 9/2011 | Shekalim |
| 8,771,229 B2 | 7/2014 | Amirouche et al. |
| 2002/0119711 A1 | 8/2002 | VanAntwerp et al. |
| 2003/0100883 A1 | 5/2003 | Kristensen et al. |
| 2003/0180164 A1 | 9/2003 | Bunner et al. |
| 2004/0050104 A1 | 3/2004 | Ghosh et al. |
| 2004/0094733 A1 * | 5/2004 | Hower ............... A61B 5/14514 251/11 |
| 2004/0176727 A1 | 9/2004 | Shekalim |
| 2005/0065500 A1 | 3/2005 | Couvillon, Jr. et al. |
| 2005/0176089 A1 * | 8/2005 | Ehrlich .................. G01N 33/66 435/40.5 |
| 2005/0192557 A1 | 9/2005 | Brauker et al. |
| 2006/0021386 A1 | 2/2006 | Wang |
| 2006/0073232 A1 | 4/2006 | Wang |
| 2006/0145372 A1 | 7/2006 | Jones et al. |
| 2006/0224109 A1 | 10/2006 | Steil et al. |
| 2007/0073230 A1 | 3/2007 | Jasperson et al. |
| 2007/0087068 A1 | 4/2007 | Eiha et al. |
| 2007/0225147 A1 | 9/2007 | Hayashi et al. |
| 2007/0233008 A1 | 10/2007 | Kristensen et al. |
| 2007/0299398 A1 | 12/2007 | Alferness et al. |
| 2008/0169444 A1 | 7/2008 | Guala |
| 2009/0062767 A1 | 3/2009 | Van Antwerp et al. |
| 2009/0069650 A1 | 3/2009 | Jennewine |
| 2009/0105658 A1 | 4/2009 | Jennewine |
| 2010/0004603 A1 | 1/2010 | Kristensen et al. |
| 2010/0081993 A1 | 4/2010 | O'Connor |
| 2010/0100077 A1 | 4/2010 | Rush et al. |
| 2010/0114008 A1 * | 5/2010 | Marchitto ............. A61M 35/00 604/20 |
| 2010/0185322 A1 | 7/2010 | Bylsma et al. |
| 2010/0225013 A1 | 9/2010 | Eiha et al. |
| 2010/0241086 A1 | 9/2010 | Yodfat et al. |

(56) References Cited

U.S. PATENT DOCUMENTS

| | | |
|---|---|---|
| 2010/0255366 A1 | 10/2010 | Myland |
| 2010/0256593 A1 | 10/2010 | Yodfat et al. |
| 2010/0280461 A1 | 11/2010 | Forstreuter |
| 2010/0317093 A1 | 12/2010 | Turewicz et al. |
| 2011/0021905 A1 | 1/2011 | Patrick et al. |
| 2011/0066131 A1 | 3/2011 | Cabiri |
| 2011/0114744 A1 | 5/2011 | Ricciardi et al. |
| 2011/0118675 A1 | 5/2011 | Miller et al. |
| 2011/0137287 A1 | 6/2011 | Gonnelli et al. |
| 2011/0160696 A1 | 6/2011 | Hoss |
| 2011/0168294 A1 | 7/2011 | Jakobsen et al. |
| 2011/0251546 A1 | 10/2011 | Sullivan et al. |
| 2011/0274566 A1 | 11/2011 | Amirouche et al. |
| 2011/0308650 A1 | 12/2011 | Amirouche et al. |
| 2011/0309229 A1 | 12/2011 | Amirouche et al. |
| 2011/0309552 A1 | 12/2011 | Amirouche et al. |
| 2012/0002422 A1 | 1/2012 | Lia et al. |
| 2012/0053571 A1 | 3/2012 | Petri |
| 2013/0144214 A1 | 6/2013 | Amirouche et al. |
| 2013/0144254 A1 | 6/2013 | Amirouche et al. |
| 2013/0237947 A1 | 9/2013 | Amirouche et al. |
| 2013/0274576 A1 | 10/2013 | Amirouche et al. |
| 2013/0274577 A1 | 10/2013 | Amirouche et al. |

FOREIGN PATENT DOCUMENTS

| | | |
|---|---|---|
| GB | 2 248 891 A | 4/1992 |
| JP | 62-297120 A | 12/1987 |
| JP | 2007-015906 A | 1/2007 |
| JP | 2007-0119280 A | 5/2007 |
| JP | 2008-96089 A | 4/2008 |
| WO | WO 03/047426 A1 | 6/2003 |
| WO | WO 2004/067864 A | 8/2004 |
| WO | WO 2006/111775 A | 10/2006 |
| WO | WO 2007/055042 A1 | 5/2007 |
| WO | WO 2009/049462 A1 | 4/2009 |
| WO | WO 2010/128914 A1 | 11/2010 |

OTHER PUBLICATIONS

"Peripheral Neuropathy Market Approaches US$1B by 2012," PR Newswire United Business Media, [Online]. Available: http://www.prnewswire.co.uk/news-releases/peripheral-neuropathy-market-approaches-us1b-by-2012-154534705.html, Apr. 7, 2012.
J. K. Richardson et al., "Peripheral Neuropathy: A True Risk Factor for Falls," The Journals of Gerontology: Series A, vol. 50, No. 4, pp. 211-215, 1995. (Abstract).
"Diabetic Neuropathy, Living With Numbness and Pain," A Diabetic Life, [Online]. Available: http://www.a-diabetic-life.com/diabetic-neuropathy.html. [Accessed May 5, 2012].
"Diabetes Basics: Diabetes Statistics," American Diabetes Association, [Online]. Available: http://www.diabetes.org./diabetes-basics/. [Accessed May 14, 2012].
"Peripheral Neuropathy Fact Sheet," National Institute of Neurological Disorders and Stroke, NIH Publication No. 04-4853, [Online]. Available: http://www.ninds.nih.gov/disorders/peripheralneuropathy/detail_peripheralneuropathy.htm. Sep. 19, 2012.
"Eiectromyogram (EMG)," Medicine.net.com, [Online]. Available: http://www.medicinenet.com/electromyogram/article.htm. [Accessed May 15, 2012].
"Nerve conduction velocity," Medline Plus, A service of the U.S. National Library of Medicine, National Institutes of Health, [Online]. Available: http://www.nlm.nih.gov/medlineplus/ency/article/003927.htm. Jun. 18, 2011.
G. C. Farnbach, "Peripheral Nerve Testing and Electromyography," [Online]. Available: hitp://cal.vet.upenn.edu/projects/saortho/appendix_d/appd.htm. [Accessed May 18, 2012].
E. J. Mundell, "Antidepressant Cymbalta Might Ease Chemo-Linked Pain," MSN Health, [Online]. Available: http://health.msn.com/health-topics/cancer/antidepressant-cymbalta-might-ease-chemo-linked-pain. Jun. 2, 2012.

B. S. Galer et al., "The Lidocaine Patch 5% Effectively Treats All Neuropathic Pain Qualities: Results of a Randomized, Double-Blind, Vehicle-Controlled, 3-Week Efficacy Study With Use of the Neuropathic Pain Scale," The Clinical Journal of Pain, vol. 18, No. 5, pp. 297-301, 2002 (Abstract).
D. A. Rosielle, "The Lidocaine Patch," Medical College of Wisconsin, [Online]. Available: http://www.eperc.mcw.edu/EPERC/FastFactsIndex/ff_148.htm [Accessed May 15, 2012].
A. R. Gammaitoni et al., "Pharmacokinetics and Tolerability of Lidocaine Patch 5% with Extended Dosing," The Annals of Pharmacotherapy, vol. 36, No. 2, pp. 236-240, 2002 (Abstract).
T. Morrow, "Transdermal Patches Are More Than Skin Deep," Managed Care, Apr. 2004. Available http://www.managedcaremag.com/archives/0404/0404.biotech.html. Apr. 2004.
F. Amirouche et al., "Current Micropump Technologies and Their Biomedical Applications," Microsystem Technologies, vol. 15, pp. 647-666, 2009.
Pending U.S. Appl. No. 13/308,699, filed Dec. 1, 2011, titled "Cartridge System for Delivery of Medicament,".
Pending U.S. Appl. No. 13/448,013, filed Apr. 16, 2012, titled "Medication Delivery Device with Multi-Reservoir Cartridge System and Related Methods of Use,".
Pending U.S. Appl. No. 13/470,140, filed May 11, 2012, titled "Medication Delivery Device and Related Methods of Use,".
Pending U.S. Appl. No. 13/370,091, filed Feb. 9, 2012, titled "Drug Delivery and Methods Therefor,".
Pending U.S. Appl. No. 13/416,249, filed Mar. 9, 2012, titled "Multi-Ported Drug Delivery Device Having Multi-Reservoir Cartridge System,".
Pending U.S. Appl. No. 13/174,643, filed Jun. 30, 2011, titled "Method of Making a Membrane for Use with a Flow Control System for a Micropump,".
Pending U.S. Appl. No. 13/174,624, filed Jun. 30, 2011, titled "Mold for Making a Membrane for Use with a Flow Control System for a Micropump,".
Pending U.S. Appl. No. 13/174,598, filed Jun. 30, 2011, titled "Flow Control System for a Micropump,".
Pending U.S. Appl. No. 13/692,868, filed Dec. 3, 2012, titled "Medicament Delivery Systems,".
"Bartels micropumps," Apr. 2009, [online] http://www.bartelsmikrotechnik.de/index.php/micropumps.html (3 pages).
"Silastic® BioMedical Grade ETR elastomers", Dow Corning, 2002-2011, accessed at http://www4.dowcorning.com/DataFiles/090007c880228669a.pdf (5 pages).
"Silastic © Biomedical Grade Liquid Silicone Rubbers", Dow Corning, 2006, accessed at http://www4.dowcorning.com/DataFiles/090007c88097f96.pdf (6 pages).
"Small, powerful, light, precise: micro diaphragm pumps made of plastics: thinXXS micropumps" Mar. 2009, [online] http://www.thinxxs.com/main/produkte/micropumps.html (2 pages).
"Sylgard® 184 Silicone Elastomer", Dow Corning, 2007, accessed at http://ncnc.engineering.ucdavis.edu/pages/equipment/Sylgard_184_data_sheet.pdf (3 pages).
Acevedo, "Creation of Dual Chamber Micropump Using Rapid Prototyping," Milwaukee School Engineering, Research Experience for Undergraduates Paper, 2005. Available online at: http://www.msoe.edu/academics/research_centers/reu/pdf/2005/Creation%20of%20a%20dual%20Chamber%20Micropump%20using%20Rapid%20Prototyping.pdf (6 pages).
Anhalt et al., "Insulin Patch Pumps: Their Development and Future in Closed-Loop Systems," *Diabetes Technology & Therpeutics*, 2010, pp. 51-58, vol. 12.
Bak et al., "Mutiple Insulin Injections Using a Pen Injector Versus Insulin Pump Treatment in Young Diabetic Patients," *Diabetes Research*, 1987, pp. 155-158, vol. 6.
Bohm et al., "A plastic micropump constructed with conventional techniques and materials," *Sensors and Actuators A*, 1999, vol. 77-3, pp. 223-228.
Casella et al., "Accuracy and Precision of Low-Dose Insulin Administration," *Pediatrics*, 1993, pp. 1155-1157, vol. 91.
Dario et al., "A fluid handling system for a chemical microanalyzer," *J. Micromech. Microeng.*, 1996, vol. 6, pp. 95-98.

(56) References Cited

OTHER PUBLICATIONS

Davis et al., "Techniques for Improved Soft Lens Fitting"; Aug. 1, 2005, p. 2, accessed at http://www.clspectrum.com/articleviewer.aspx?articleid=12852 (5 pages).

Einhorn et al., "Advances in Diabetes for the Millennium: Insulin Treatment and Glucose Monitoring," *Medscape General Medicine*, 2004, p. 6, vol. 6, (3 Suppl.) [Online]. Available at: http://www.medscape.org/viewarticle/488996 (9 pages).

Elleri et al., "Closed-Loop Insulin Delivery for Treatment of Type 1 Diabetes," *BMC Medical*, 2011, p. 120, vol. 9 [Online]. Available at: http://www.biomedcentral.com/1741-7015/9/120 (9 pages).

Fu et al. "TiNi-based thin films in MEMS applications: a review," *Sensors and Actuators A*, 2004, pp. 395-408, vol. 112, No. 23.

Ha et al., "Disposable thermo-pneumatic micropump for bio lab-on-a-chip application," *Microelectronic Engineering*, 2009, pp. 1337-1339, vol. 86.

Ignaut et al., "Comparative Device Assessments: Humalog KwikPen Compared with Vial and Syringe and FlexPen," *The Diabetes Educator*, 2009, pp. 789-798, vol. 35, No. 2.

International Search Report and Written Opinion issued in International Patent Application No. PCT/US2009/059020, dated Mar. 9, 2010 (17 pages).

International Search Report and Written Opinion issued in International Patent Application No. PCT/US2012/066937, dated Mar. 7, 2013 (7 pages).

International Search Report and Written Opinion issued in International Patent Application No. PCT/US2013/035918, dated Jun. 21, 2013 (9 pages).

International Search Report and Written Opinion issued in International Patent Application No. PCT/US2013/035921, dated Jul. 1, 2013 (11 pages).

International Search Report and Written Opinion issued in International Patent Application No. PCT/US2013/046546, dated Aug. 8, 2013 (11 pages).

Irawan et al., "Fabrication and performance testing of disposable micropump suitable for microfluidic chip," in Intl. Conf. on Biomedical and Pharmaceutical Engineering, Orchard Hotel, Singapore, Dec. 2006, pp. 252-255.

Jeong et al. "Fabrication of a peristaltic PDMS micropump," *Sensors and Actuators A*, 2005, pp. 453-458, vol. 123-124.

Junwu et al., "Design and test of a high-performance piezoelectric micropump for drug delivery," *Sensors and Actuators A*, 2005, vol. 121, pp. 156-161.

Klonoff et al., "Insulin Pump Safety Meeting: Summary Report," *Journal of Diabetes Science and Technology*, 2009, pp. 396-402, vol. 3, No. 2.

Koch, et al., "PDMS and tubing-based peristaltic micropumps with direct actuation," *Sensors and Actuators B*, vol. 135, pp. 664-670, 2009.

Laser et al., "A review of micropumps," *J. Micromech. Microeng.*, vol. 14(6), pp. R35-R64, 2004.

Lee et al., "Microfluidic mixing: A review," *Int. J. Mol. Sci.*, 2011, pp. 3263-3287, vol. 12.

Li et al., "A high frequency high flow rate piezoelectrically driven MEMS micropump" in Proceedings IEEE Solid State Sensors and Actuators Workshop, Hilton Head, SC, Jun. 2000 (4 pages).

Ma et al., "Development and application of a diaphragm micropump with piezoelectric device," *Microsyst. Technol.*, vol. 14, pp. 1001-1007, 2008.

Manz, et al., "Miniaturized total chemical analysis systems: a novel concept for chemical sensing," *Sensors and Actuators B*, vol. 1, pp. 244-248, 1990.

Meece et al., "Effect of Insulin Pen Devices on the Management of Diabetes Mellitus," *Am. J. Health-Syst. Pharm.*, 2008, pp. 1076-1082, vol. 65.

Melin et al., "A fast passive and planar liquid sample micromixer." *Lab on a Chip*, 2004, pp. 214-219, vol. 4.

Nguyen et al., "MEMS-micropumps: a review," *Journal of Fluids Engineering*, vol. 124, p. 384-392, 2002.

Nguyen et al., "Microfluidics for Internal Flow Control: Micropumps," in *Fundamentals and Applications of Microfluidics*. Norwood, MA: Artech House, Inc., 2002: pp. 293-341.

Nisar et al., "MEMS-based Micropumps in Drug Delivery and Biomedical Applications," *Sensors and Actuators B*, 2008, pp. 917-942, vol. 130.

Pallikaris, "Intracorneal micro-lens a minimally invasive option for presbyopia"; Aug. 10, 2010, p. 1, paragraph 003, accessed at http://www.rigneygraphics.com/clients/presbia/website/newsmedia/pdfs/press-osn-presbia.pdf (2 pages).

Pan et al, "A magnetically driven PDMS micropump will ball check-valves," *J. Micromech. Microeng*, 2005, vol. 15, pp. 1021-1026.

Rapp et al., "Liga micropump for gases and liquids," *Sensors and Actuators A*, 1994, pp. 57-61, vol. 40, No. 1.

Roberts, "Blind Attack on Wireless Insulin Pumps Could Deliver Lethal Dose," Threatpost.com, The Kaspersky Lab Security News Service, Oct. 27, 2011 (2 pages).

Santra et al., "Fabrication and testing of a magnetically actuated micropump," *Sensors and Actuators B*, vol. 87, pp. 358-364, 2002.

Selam, "Evolution of Diabetes Insulin Delivery Devices," *Journal of Diabetes Science and Technology*, 2010, pp. 505-513, vol. 4, No. 3.

Shen et al., "Minaturized PMMA ball-valve micropump with cylindrical electromagnetic actuator," *Microelectric Engineering*, vol. 85, pp. 1104-1107, 2008.

Singhal et al., "Microscale pumping technologies for microchannel cooling systems," *Appl. Mech. Rev.*, vol. 57(3), pp. 191-221, 2004.

Star Micronics Co. Ltd., "Precision products," Mar. 2009, [online]. Accessed at: http://www.star-m.jp/eng/products/precision/index/html, on Aug. 22, 2011 (4 pages).

Trenkle et al., "Normally-closed peristaltic micropump with reusable actuator and disposable fluidic chip," *Sensors and Actuators B*, vol. 154, pp. 137-141, 2011.

Tsai et al., "Review of MEMS-based drug delivery and dosing systems," *Sensors and Actuators A*, vol. 134, No. 2, pp. 555-564, 2007.

U.S. Appl. No. 13/174,598, filed Jun. 30, 2011, by Amirouche et al.: Non-Final Rejection, dated May 14, 2013.

U.S. Appl. No. 13/174,598, filed Jun. 30, 2011, by Amirouche et al.: Final Rejection, dated Oct. 3, 2013.

U.S. Appl. No. 13/174,624, filed Jun. 30, 2011, by Amirouche et al.: Non-Final Rejection, dated Jun. 28, 2012.

U.S. Appl. No. 13/174,624, filed Jun. 30, 2011, by Amirouche et al.: Final Rejection, dated Nov. 21, 2012.

U.S. Appl. No. 13/174,624, filed Jun. 30, 2011, by Amirouche et al.: Non-Final Rejection, dated Feb. 8, 2013.

U.S. Appl. No. 13/174,624, filed Jun. 30, 2011, by Amirouche et al.: Final Rejection, dated Jul. 31, 2013.

U.S. Appl. No. 13/174,643, filed Jun. 30, 2011 by Amirouche et al.: Non-Final Rejection, dated May 2, 2013.

U.S. Appl. No. 13/174,643, filed Jun. 30, 2011 by Amirouche et al.: Notice of Allowance, dated Oct. 21, 2013.

U.S. Appl. No. 13/308,899, filed Dec. 1, 2011 by Amirouche et al.: Non-Final Rejection, dated Aug. 8, 2013.

U.S. Appl. No. 13/370,091, filed Feb. 9, 2012 by Amirouche et al.: Non-Final Rejection, dated Aug. 21, 2013.

Van Lintel, et al., "A piezoelectric micropump based on micromachining of silicon," *Sensors and Actuators A*, 1988, vol. 15, p. 153-167.

Yadav et al., "Various Non-Injectable Delivery Systems for the Treatment of Diabetes Mellitus," *Endocrine, Metabolic & Immune Disorders—Drug Targets*, 2009, pp. 1-13, vol. 9, No. 1.

Yamahata et al. "A PMMA valveless micropump using electromagnetic actuation," *Microfluid Nanofluid*, 2005, vol. 1, pp. 197-207.

Zhu et al., "Optimization design of multi-material micropump using finite element method," *Sensors and Actuators A*, 2009, vol. 149, pp. 130-135.

International Search Report and Written Opinion issued in International Patent Application No. PCT/US2013/072787, dated Apr. 24, 2014 (9 pages).

U.S. Appl. No. 13/174,598, filed Jun. 30, 2011, by Amirouche et al.: Notice of Allowance, dated Apr. 7, 2014.

(56) References Cited

OTHER PUBLICATIONS

U.S. Appl. No. 13/174,624, filed Jun. 30, 2011, by Amirouche et al.: Notice of Allowance, dated Feb. 5, 2014.
U.S. Appl. No. 13/303,899, filed Dec. 1, 2011, by Amirouche et al.: Notice of Allowance, dated Feb. 28, 2014.
U.S. Appl. No. 13/174,598, filed Feb. 9, 2012, by Amirouche et al.: Notice of Allowance, dated Mar. 25, 2014.

* cited by examiner

MEDICAMENT DISTRIBUTION SYSTEMS AND RELATED METHODS OF USE

I. CROSS-REFERENCE RELATED APPLICATION

This patent application claims the benefits of priority under 35 U.S.C. §§ 119-120 to U.S. Provisional Application No. 61/664,516, filed on Jun. 26, 2012, the entirety of which is incorporated herein by reference.

II. DESCRIPTION

Field of the Disclosure

Embodiments of the present disclosure relate to, among other things, the field of medical devices and, in particular, to devices for the delivery and/or distribution of one or more substances, such as, e.g., medicaments, to a patient by, for example, topical and/or subcutaneous delivery. More specifically, embodiments of the present disclosure are directed to a medicament delivery and/or distribution system that utilizes, among other things, a pump and a patch, featuring, e.g., a multi-array tray, to deliver, e.g., medicament from the distribution system to a patient.

Embodiments of the present disclosure also relate to a medicament delivery and/or distribution system having a feedback control and/or outcome indicator mechanism. The system may include one or more electrodes and may use nerve conduction velocity (NCV), electromyography (EMG), or both, to aid in receiving feedback from or delivering a dose of medicament to a patient.

Background of the Disclosure

Peripheral Neuropathy (PN) is a condition that affects millions of people in the United States, PN affects the nervous system and, in particular, the peripheral nerves. The peripheral nerves in the body resemble a communications network, transmitting information from the brain and spinal cord (which form a portion of the central nervous system) to the rest of the body. Each peripheral nerve has a specialized purpose depending on its location. PN is considered a progressive disease and involves the slow, gradual decline of the peripheral nerves, causing painful tingling and burning, muscle weakness, sensory nerve damage, cramping, and bone degeneration as some of its symptoms. Currently, there is no cure or preventative treatment for this disease.

The peripheral nerves can be damaged or may deteriorate for a number of reasons, including, but not limited to, genetics; physical injury or trauma; systemic diseases, such as diabetes, AIDS, and lupus; kidney disorders; hormonal imbalances; vitamin deficiencies; alcoholism; vascular damage and blood diseases; connective tissue disorders and chronic inflammation; cancers and benign tumors; repetitive stress; toxins; infections and autoimmune disorders; Lyme disease; diphtheria; and viral and bacterial infections.

PN affects men and women equally and can occur in older adults, aged approximately 55 to 60 years old. PN is a contributing factor for hip fractures and one of the leading causes of falls in seniors. The complications of PN may be especially troublesome for diabetics and cancer patients who have received chemotherapy. PN can be a cause of surgical amputation for diabetic neuropathy patients, accounting for almost 100,000 procedures annually. Diabetics may commonly have a painful and severe PN. About 60 to 70% of people with diabetes usually experience mild to severe PN, and with nearly 26 million diabetics in the U.S., that number could equal nearly 15 to 18 million. The Centers for Disease Control and Prevention projects that diabetes cases will double, or even triple, by 2050.

Diagnosing PN may be difficult, because the symptoms mimic many other diseases and conditions. A patient suspected of having PN may undergo a thorough neurological examination, and the doctor could review, among other things, lifestyle choices, work background, exposure to toxins, family history of neurological disease, alcohol abuse, and other risk factors. The patient may be tested for diabetes, vitamin deficiencies, liver or kidney dysfunction, other metabolic disorders, abnormal immune system activity, blood or cardiovascular diseases, connective tissue disorders, and malignancies, amongst others. Two available tests may more accurately indicate muscle and nerve function. An EMG test, e.g., may detect abnormal muscle electrical activity, and an NCV test may measure how fast electrical impulses are travelling. The tests may work because electrical signals may travel more slowly across damaged nerves.

When it comes to treating PN, there are a number of prescription medications and over-the-counter options available. In some cases, treatment may include prescribing an acetaminophen, such as Tylenol®, or non-steroidal anti-inflammatories, like Advil® or Motrin®. Some doctors prescribe anti-depressants, for instance, the drug Cymbalta® has been shown to relieve PN symptoms. Doctors may also prescribe anti-seizure medications (anti-convulsants or anti-epileptics), and/or other opioids (narcotics). PN may also be treated topically. For instance, creams, ointments, gels, lotions, and/or patches can be applied directly to the skin to provide relief from nerve pain and inflammation. The two main types of topical medications available include anesthetics and analgesics. Local anesthetics, such as the Lidocaine patch and EMLA cream, treat localized pain by numbing the area and blocking the pain where applied. Analgesics are nonprescription topical pain relievers that are applied to the skin. They are made of capsaicin, which may be found in the seeds of hot chili peppers, and work by reducing the ability of nerve cells to transmit messages to the brain. They may be sold commercially as Capzasin-P, Dolorac, Zostrix, and others.

The currently available treatments have many disadvantages. Some patients are unable to tolerate swallowing pills. Some oral medications, such as opioids, may cause numerous adverse effects, including nausea, constipation, sedation, cognitive impairment, falling, or addiction. The anti-seizure medication gabapentin can cause somnolence, dizziness, edema, and gastrointestinal symptoms. Tri-cyclic antidepressants must be used cautiously in patients with a history of cardiovascular disease, glaucoma, or urinary retention, and they may cause weight gain, dry mouth, balance problems, and more. Accordingly, there exists a need for better treatment options for PN patients. The present disclosure offers a medicament distribution system that will act as an alternative to the current treatment, including the simple Lidocaine patches currently available on the market. The current patches can be overloaded with medications and may expose the skin to excess medication all at once, causing irritations, and skin rashes. Further, the current Lidocaine patch treatment is static because it is unable to control or determine how much or at what rate the medicine is being absorbed into the skin.

The present disclosure proposes a medicament distribution system for treating symptoms and diseases, e.g., PN, at an affordable cost that may utilize less medication and may provide dosage control. Embodiments of the present disclosure may be able to deliver medication to an area of the body, for instance, the skin, in, e.g., a precise and timed manner, in order to enhance the effectiveness of drug absorption. In addition, in some embodiments, the disclosed embodiments may also contain a suitable nerve conduction velocity testing system, or any other suitable diagnostic mechanism (e.g., myography), that has the unique ability to continuously monitor the receptiveness of the patient's nerves, allowing for adjustable closed-loop dosing.

Embodiments of the disclosure described herein may overcome some disadvantages of the prior art by providing a medicament distribution system, featuring a patch, a pump, and in some embodiments, continuous monitoring and/or feedback testing, such as nerve damage testing, e.g., NCV and EMG.

III. SUMMARY OF THE DISCLOSURE

Embodiments of the present disclosure relate to medical devices, and more particularly, to devices for releasing a medicament to the body of a wearer. Various embodiments of the disclosure may include one or more of the following aspects.

In accordance with one embodiment, a medical device for releasing a medicament may include a multi-layer patch. The patch may include a base layer configured to secure the patch to a body of a user and a medicament array located adjacent the base layer. The array may include a plurality of wells configured to release a quantity of medicament from the array to the body of the user. The device may also include a cover layer located on a side of the medicament array opposite the base layer and a pump operably coupled to the patch and configured to deliver a quantity of fluid to the patch.

Various embodiments of the adaptor may include one or more of the following features: the multi-layer patch may include a membrane located between the cover layer and the medicament array, and the cover layer and the membrane may define a cavity configured to hold the quantity of fluid, and the membrane may be configured to deform into the plurality of wells in response to an increased volume of fluid in the cavity; the cover layer may include at least one port connecting an inner region of the cover layer with an outer region of the cover layer, wherein the port is configured to receive a catheter to operably connect the multi-layer patch to the pump; the cover layer may include two ports and the medical device may be configured to release more than one type of medicament; the pump may be located adjacent to the multi-layer patch; the fluid released from the pump to the multi-layer patch may include one or more medicaments; the pump may include a cartridge configured to store the one or more medicaments; the patch may include a removable seal adjacent the base layer, wherein removal of the seal exposes an adhesive for securing the multi-layer patch to the body of the user; the medicament array may be pre-filled; and the medical device may include a programmable controller.

In accordance with another embodiment, a medical device for releasing a medicament may include a patch having a medicament array with a plurality of wells configured to release a quantity of medicament from a storage region of the wells to a body of a user. The device may further include a pump operably coupled to the patch and configured to deliver a quantity of fluid from the pump to a region above the storage region of the wells. The wells may be configured to release a quantity of medicament to the body in response to an increase in the amount of fluid delivered from the pump. The device may also include a controller operably coupled to the pump and one or more sensors configured to measure one or more body parameters. The sensors may be configured to relay information about the body parameters to the controller.

Various embodiments of the medical device may include one or more of the following features: the patch may include a membrane adjacent the medicament array and configured to deform into the plurality of wells in response to the increase in the amount of fluid delivered from the pump; the controller may be configured to adjust the amount, timing, or type of fluid delivered from the pump to the patch based on the information received from the one or more sensors; the one or more sensors may be two electrodes, and the body parameter may be the electrical activity of one or more nerves or muscles; and the one or more sensors may be configured to continuously monitor the body parameter.

In accordance with another embodiment, the medical device for releasing a medicament may include a patch having a medicament array with a plurality of wells configured to release a quantity of medicament from the array to a body of a user. The patch may also include a membrane located adjacent the plurality of wells and configured to deform into the plurality of wells. The device may further include a mechanism to secure the patch to the body of the user and a pump configured to deliver a quantity of fluid to the patch, wherein the delivery of fluid increases the pressure on the membrane, causing the wells to release the quantity of medicament to the body of the user. The medical device may also include a controller configured to control the delivery of fluid from the pump to the patch.

Various embodiments of the medical system may include one or more of the following features: the controller may be a programmable logic controller; the controller may be wirelessly coupled to an input device and configured to receive input from a remote user; the medicament array may be configured to contain and release a plurality of medicaments; and the medicament array may be configured to release a first medicament of the plurality of medicaments at a first rate and to release a second medicament of the plurality of medicaments at a second rate, wherein the second rate is different from the first rate.

IV. BRIEF DESCRIPTION OF THE DRAWINGS

The accompanying drawings illustrate certain exemplary embodiments of the present disclosure, and together with the description, serve to explain principles of the present disclosure.

V. DETAILED DESCRIPTION OF THE PREFERRED EMBODIMENTS

Reference will now be made in detail to the exemplary embodiments of the present disclosure described below and illustrated in the accompanying drawings. Wherever possible, the same reference numbers will be used throughout the drawings to refer to same or like parts.

While the present disclosure is described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the invention. Accordingly, the disclosure is not to be considered as limited by the foregoing or following descriptions.

Other features and advantages and potential uses of the present disclosure will become apparent to someone skilled in the art from the following description of the disclosure, which refers to the accompanying drawings.

Prior to providing a detailed description of the embodiments disclosed herein, however, the following overview is provided to generally describe the contemplated embodiments. Further, although the embodiments disclosed herein are described in connection with the distribution of, e.g., skin medicaments for PN, those of ordinary skill in the art will understand that any suitable therapeutic or diagnostic agent may be delivered to a patient, regardless of whether the agent is delivered to treat a disease state. Further, although the embodiments disclosed herein are described in connection with the measurement of, e.g., body parameters such as nerve or muscle conductivity, one of skill in the art will recognize that the principles of the present disclosure may be suitable for measuring any body parameter, including, e.g., electrocardiograms, blood pressure, cholesterol levels, blood sugar levels, sodium levels, medicament saturation levels, and so forth. For example, the embodiments disclosed herein may deliver medicaments for pain management or joint lubrication, or may be used for reverse controlled fluid extraction. Commercial applications may include, e.g., home care, hospital, nursing homes, military, and the battlefield.

Certain disclosed embodiments relate to a system of medicament distribution and, among other things, a continuous feedback monitoring device. The term "fluid" may include a state of matter or substance, liquid or gas, whose particles can move about freely and have no fixed shape, but rather conform to the shape of their containers. The term "cavity" may include a space or passage for fluids to flow through or within. The term "medicament" may be used to refer to a substance used in therapy, a substance that treats, prevents, or alleviates the symptoms of disease, a medicine in a specified formulation, an agent that promotes recovery from injury or ailment, or any other fluid used in the treatment or diagnosis of a patient.

Figure 1:
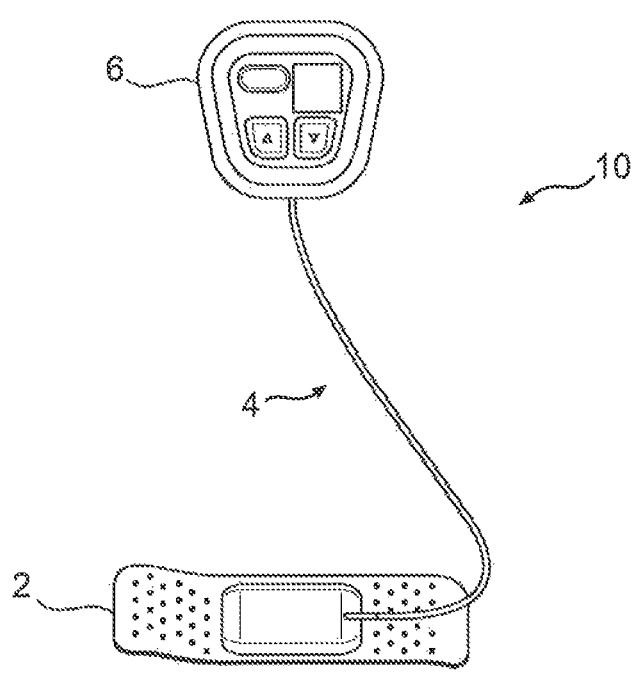
FIG. 1 depicts a perspective view of an exemplary medicament distribution device, in accordance with an embodiment of the present disclosure.
Figure 2A:
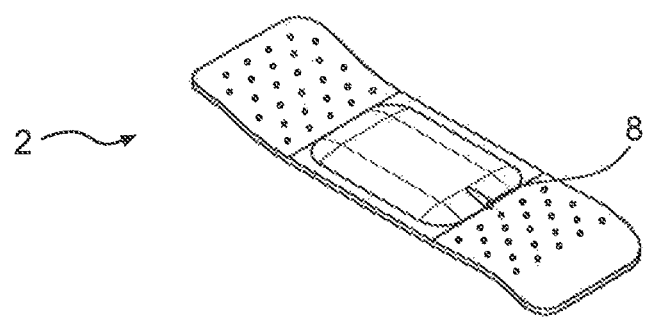
FIG. 2A depicts a perspective view of an exemplary device of FIG. 1.
Figure 2B:
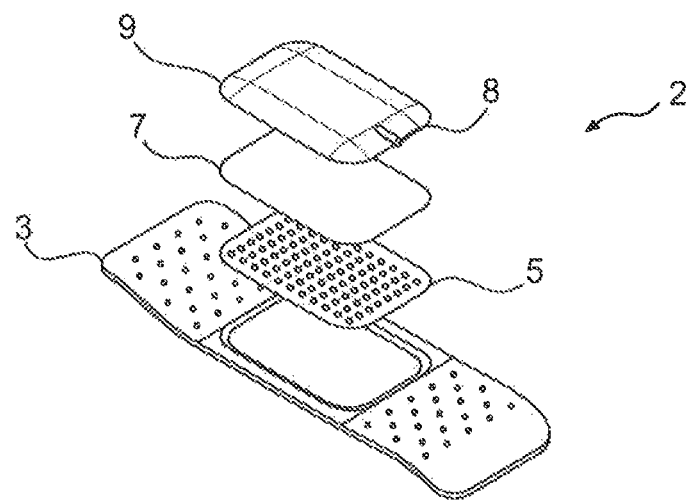
FIG. 2B depicts an exploded view of the exemplary device of FIG. 2A.

In the embodiment depicted in FIG. 1, a medical device 10 for delivering a medicament to the body of a user may include a multi-layer patch 2 configured to contain and deliver medicament. As seen in FIG. 2, patch 2 may include a base layer 3, a medicament array layer 5, a membrane layer 7, and a cover layer 9. Patch 2 may be any suitable size, width, shape, color, or configuration. For instance, FIGS. 1, 2, 6 and 7 show different shapes and configurations of patches, including, for example, circular and rectangular embodiments. Additionally, patch 2 may be irregularly shaped, triangular, oval, hour-glass shaped, or may be any other suitable shape. Patch 2 may also come in any size, depending on the size and/or location of the area to which medicament must be delivered. Patch 2 may have designs, colors, shapes, or logos to appeal to children or adults. For instance, patch 2 may come in a number of shades so as to be inconspicuous and allow for closely matching a wearer's skin color. In other embodiments, patch 2 may include images, such as characters, patterns, writing, or team logos, for instance.

Patch 2 and its components may be formed of any suitable materials. Patch 2 may resemble an adhesive bandage, a medical patch, or any other skin-covering device, and may be formed of a suitable plastic or polymer, such as, e.g., silicone, acrylic, rubber, or natural fiber, or any combination of materials. Patch 2 may be, e.g., hypoallergenic, biocompatible, permeable to air, or impermeable to air, depending on the type of medicament 16 to be delivered by patch 2. In addition, patch 2 or certain layers of patch 2 may be waterproof. In some embodiments, patch 2 may be flexible to allow base layer 3 to move with the patient. In other embodiments, patch 2 may be hard, rigid, or inflexible to offer protection to the underlying area.

Base layer 3 of patch 2 may be configured to directly contact the body of a patient, for instance, e.g., on the skin. Base layer 3 may be configured to retain patch 2 on the wearer for any amount of time, for example, temporarily or for prolonged use. Base layer 3 may be held onto the wearer via any suitable means, for instance, with adhesive, such as glue or tape; a strap to wrap around a portion of the body, for instance, an elastic, Velcro®, hook-and-eye, snap-on, or lace-up strap, for example. Further, in some embodiments, base layer 3 may include a larger band, glove, sock, or other wearable configuration, to wrap around an arm or leg, for instance. Such an embodiment may be preferable if distributing medicament to a larger area of the body.

Base layer 3 may be formed of any suitable material. Base layer 3 may resemble an adhesive bandage, and may be formed of a suitable plastic or polymer, e.g., silicone, acrylic, rubber, or natural fiber. Base layer 3 may be formed of hypoallergenic or biocompatible material, or may be permeable to air or may be impermeable to air depending on the medicament to be delivered by patch 2. In addition, base layer 3 may be waterproof. In some embodiments, base layer 3 may be flexible to allow base layer 3 and patch 2 to move with the patient. In other embodiments, base layer 3 may be hard, rigid, or inflexible to offer protection to the underlying area. Base layer 3 can have any suitable size, width, shape, color, or configuration.

Base layer 3 may be configured to receive medicament array 5 over a portion of base layer 3 or over the entire base layer 3. Medicament array 5 may be configured to hold or receive an amount of medicament. In one embodiment, base layer 3 of patch 2 may include a gauze or gauze-like portion onto which medicament array 5 sits. This may provide separation between the patient's skin and medicament array 5. In this embodiment, medicament from medicament array 5 may be released onto the gauze-like area of base layer 3, which may absorb some of the medicament so as to lessen the amount of medicament in direct contact with the patient. Additionally, this embodiment may help to keep the medicament in contact with the patient longer and/or may help the medicament to absorb more slowly, for instance, by keeping the contact area moistened with the medicament-soaked gauze-like section of base layer 3.

In another embodiment, medicament array 5 may rest in an open area of base layer 3 and may contact the skin directly. In this embodiment, a portion of medicament array 5 may not sit on top of base layer 3, but instead, may contact the patient along with base layer 3. In one embodiment, medicament array 5 may be elevated up off of the patient's skin so as to prevent prolonged, direct contact with the skin. Additionally, a portion of the medicament array 5 may rest on top of base layer 3, while another portion of medicament array 5 may sit substantially flush with base layer 3 directly on the patient.

In another embodiment, protective seal 1 (shown, for example, in FIGS. 7 and 8) may be located on a lower region of patch 2, for instance, under medicament array 5 and/or under base layer 3. Protective seal 1 may be configured to cover the underside of base layer 3 and/or the underside of medicament array 5. Protective seal 1 may be used to protect medicament array 5 or base layer 3 and keep medicament array 5 or base layer 3 sterile prior to or during use. Protective seal 1 may also help keep the medicament in medicament array 5 in place before or during use. For example, when patch 2 is transported from a place of manufacturing to a distribution center, e.g., a store, and then to the patient. Before use, the patient may simply remove, e.g., peel, slide, or rip, protective seal 1 from patch 2, for instance, by engaging a removal tab on protective seal 1. In one embodiment, removing protective seal 1 may also expose one or more means of affixing patch 2 to the body. For instance, removing protective seal 1 may expose an adhesive, for instance, a biocompatible stick-to-skin adhesive, which can then be attached topically to the patient in the desired location.

Figure 3A:
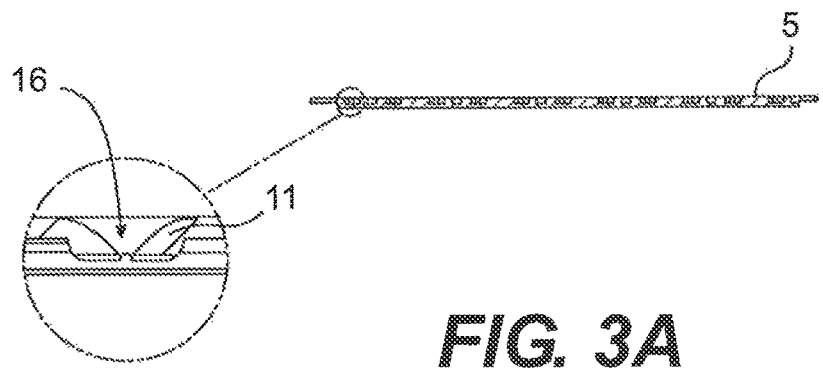
FIG. 3A depicts a cut-away view of an exemplary medicament array of the device depicted in FIG. 1.
Figure 3B:
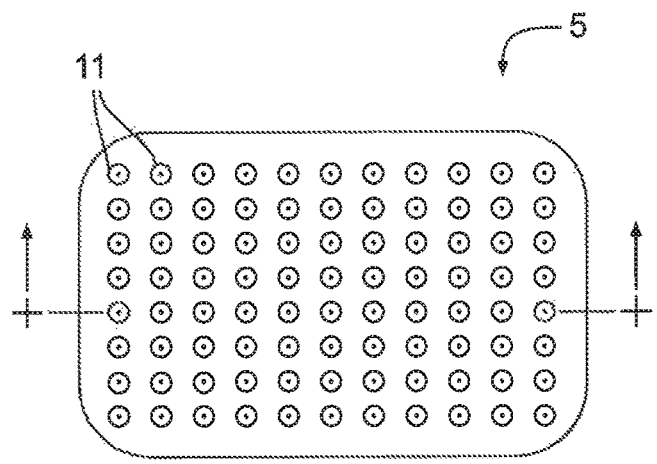
FIG. 3B depicts a top view of the exemplary medicament array of the device depicted in FIG. 3A.
Figure 3C:
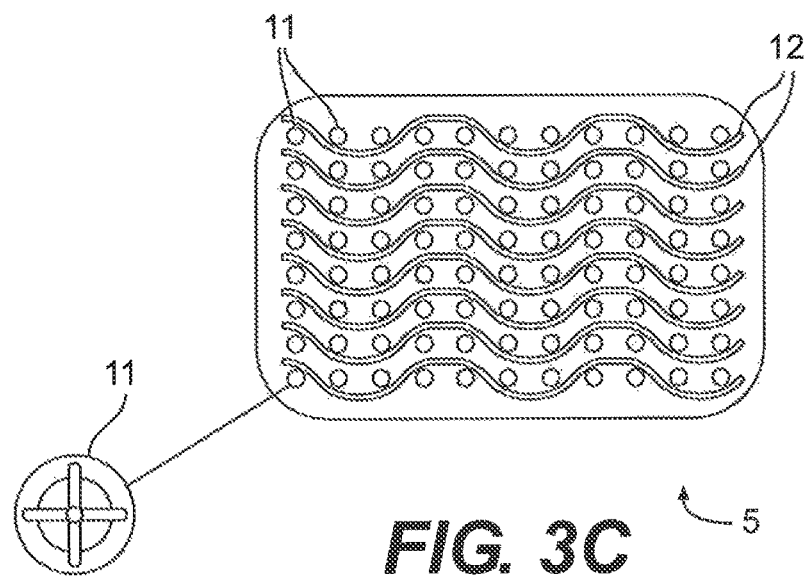
FIG. 3C depicts a bottom view of the exemplary medicament array of the device depicted in FIG. 3A.

Medicament array 5 may include a plurality of wells 11 configured to contain an amount of medicament 16, as shown in FIGS. 3 and 4. Medicament 16 may be pre-loaded in wells 11, e.g., in a disposable embodiment, or may be refillable, e.g., in either a disposable or a reusable embodiment. For instance, wells 11 of medicament array 5 may be empty and may be configured to receive medicament 16 from a source external to patch 2, for instance, from pump 6 or some other suitable dispensing device. In another embodiment, patch 2 may be pre-filled and may be disposable and replaceable upon emptying, or may be refillable. Medicament array 5 may contain any suitable number, shape, size, or configuration of wells 11. For instance, wells 11 may be evenly spaced (as shown in FIGS. 3 and 4), clustered, arranged into patterns, or irregularly scattered across medicament array 5. Wells 11 may be uniform or non-uniform, for example, in shape, size, depth, location, material, flexibility, medicament release mechanism, or configuration. Wells 11 may be configured to hold the same type of medicament 16 in each well 11 or may hold different types of medicaments 16, as discussed further below. In some embodiments, there may be a connection between the individual wells 11, allowing some movement of medicament 16 between the wells. In other embodiments, each well 11 may be isolated from each other on medicament array 5. In other embodiments, some wells 11 may be connected while others are isolated. For instance, if wells 11 are configured to hold different types of medicaments 16, wells 11 may be connected or isolated depending on whether the medicament may be mixed before delivery or kept separate.

Figure 4A:
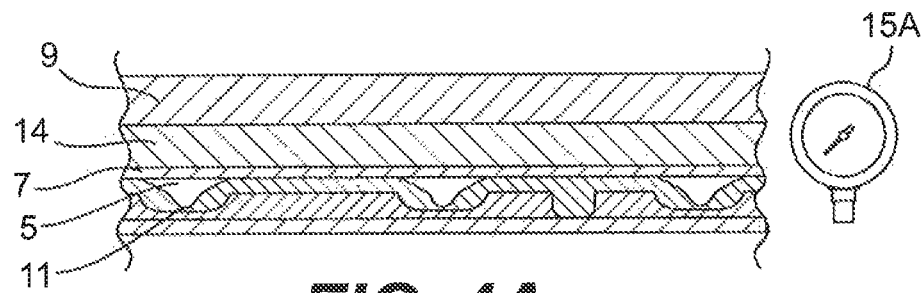
FIG. 4A depicts a cut-away view of the exemplary medicament array of the device depicted in FIG. 3A in a first configuration.
Figure 4B:
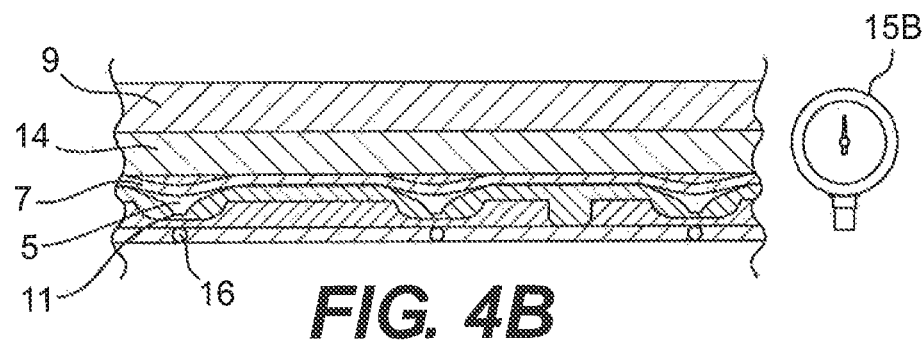
FIG. 4B depicts a cut-away view of the exemplary medicament array of the device depicted in FIG. 3A in a second configuration.
Figure 4C:
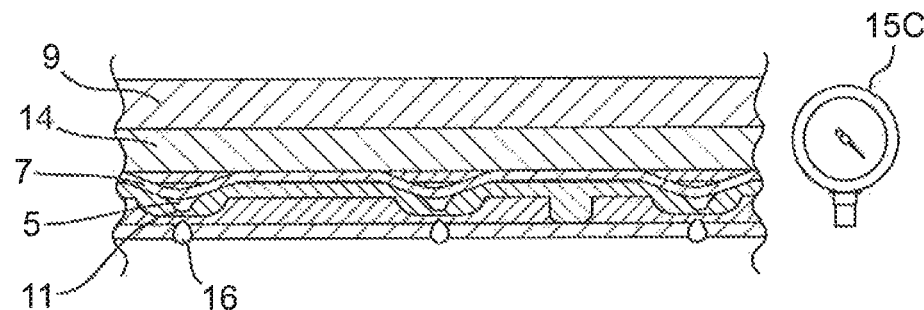
FIG. 4C depicts a cut-away view of the exemplary medicament array of the device depicted in FIG. 3A in a third configuration.

Medicament array 5 may be any suitable size, shape, or configuration. Medicament array 5 may cover the entire base layer 3 or may cover only a portion of base layer 3. Wells 11 may extend over the entirety of medicament array 5, or may cover only a portion of medicament array 5. Wells 11 may be cone-shaped, frustum-shaped, semi-circular, pear-shaped, or may include any suitable shape and size for storing and delivering a fluid. In one embodiment, a medicament distribution system 10 may utilize a medicament array 5 formed of a multi-array of frustums and/or cone-shaped wells 11 for distribution of medicament 16. Wells 11 may be configured to be substantially closed and/or impervious to fluid in some configurations, while in other configurations, wells 11 may allow medicament 16 to flow out of wells 11 and into/through base layer 3 to deliver medicament 16, as shown in FIGS. 4A-4C. For example, wells 11 may be configured to expand, become permeable, and/or open when exposed to an increase in pressure.

Medicament array 5 may be configured so that wells 11 do not come into direct contact with the skin of a wearer. Such an embodiment may be desirable for the delivery of medicament 16, so that the well openings do not become covered or blocked by the patient's body, obscuring the flow of medicament 16. Allowing space between the bottom region of wells 11 where medicament 16 may exit and the patient's skin, for example, may allow medicament 16 to flow from wells 11 more easily. The openings in wells 11 may also be designed to reduce blockages, for instance, by only allowing medicament 16 to be released with sufficient pressure from inside the medicament array. Elevating wells 11 off of the patient's skin may help wells 11 to become blocked less frequently, and may reduce irritating the patient's skin through direct contact, or through contacting medicament 16 with the skin for unnecessarily long periods of time. Additionally, if wells 11 open or expand as the medicament is released, direct contact with the patient may cause wells 11 to inadvertently pinch the wearer as medicament delivery ceases and the wells return to a closed, non-delivering position.

Medicament array 5 and/or base layer 3 may have any suitable configuration to elevate some or all of wells 11 off of the patient to avoid direct contact with, e.g, the skin. For instance, as shown in FIG. 3, a lower region of medicament array 5 may be uneven. For instance, a bottom region of medicament array 5 may have spacer waves 12, ridges, rounded structures, grids, or any other suitable shape, projections, or configuration. In other embodiments, however, a bottom region of medicament array 5 may be configured to contact the patient. For instance, in some embodiments, it may be preferable for the skin to become irritated before releasing medicament 16 onto the treatment area. In such an embodiment, a bottom region of medicament array 5 may include sharp or rough projections or a roughened contacting surface designed to contact the patient.

Medicament array 5 may be formed in any suitable manner. In one embodiment, medicament array 5 may be formed by injection molding, for instance. For example, a material, e.g., a bio-compatible liquid silicone rubber; a polymer, including thermoplastics, thermosets, or elastomers; or any other suitable substance, may be injected into a mold, e.g., a micro-patterned mold. Once cured, medicament array 5 may be flexible or rigid, depending on the materials used, and may be durable. For instance, silicone rubber may provide the resilience required for repeated opening/closing cycles of wells 11, and may prove cost effective for use in a disposable patch, for instance. This manufacturing technology may also lend itself to mass production.

Patch 2 may also include membrane layer 7. Membrane 7 may be situated on top of medicament array 5 and may be configured to cover the upper portion of wells 11. Membrane layer 7 may extend over the entire upper portion of medicament array 5, or may only extend over a portion of medicament array 5 containing one or more wells 11.

A cover 9 may be situated on top of membrane layer 7. There may be a cavity 14 (shown in FIG. 4) located between an upper portion of membrane 7 and an inner portion of cover 9. Cavity 14 may be configured to hold fluid—either a gas, a liquid, or both. Cavity 14 may also be configured to allow fluid to flow into or out of cavity 14. A port 8 may allow cavity 14 to connect to pump 6, located external to cavity 14, and in some embodiments, external to patch 2. For instance, a connector 4, such as a catheter, may operably couple port 8 and pump 6. Pump 6 may be worn on the body of the patient, on the clothes of the patient, or with patch 2, for instance.

Delivery of medicament 16 may be controlled by pump 6 by adjusting the pressure within upper cavity 14 of patch 2, which in turn controls membrane 7 adjacent medicament array 5. Pump 6 may be configured to increase or decrease the pressure in cavity 14, by, for instance, increasing or decreasing the amount of fluid in or flowing through cavity 14. Pump 6 may pump any suitable fluid into cavity 14, for instance a liquid, e.g., water, or saline, or any suitable gas, for instance, air, or hydrogen. Medicament delivery system 10 may be configured so that when pump 6 increases the pressure inside cavity 14, e.g., by increasing the amount of fluid in cavity 14, the fluid in cavity 14 applies pressure to membrane 7, causing membrane 7 to deform. Membrane 7 may be configured to deform such that membrane 7 presses down onto wells 11 in medicament array 5, increasing the pressure in wells 11, and causing medicament 16 contained in wells 11 to exit the wells. Medicament 16 may exit wells 11 through openings that may form at a bottom region of wells 11 near the patient. Accordingly, the deformation of membrane 7 may control the delivery of medicament 16 to the skin.

FIG. 4A shows membrane 7 in an un-deformed state, situated below cavity 14 and above wells 11 containing medicament 16. FIG. 4B depicts an increased-pressure configuration, in which membrane 7 has deformed so as to depress into wells 11, causing some medicament 16 to exit wells 11. In FIG. 4C, increased pressure has caused membrane 7 to deform further into wells 11, causing medicament 16 to be released from medicament array 5. Medicament 16 may drip, flow, squirt, project, spray, or otherwise exit wells 11 for delivery of medicament 16 to a patient. Wells 11 may further include valves, nozzles, nipples, droppers, or any other suitable means of regulating the flow of medicament 16 out of wells 11 and onto a patient.

In some embodiments, medicament 16 may be released from wells 11 via nozzles. In this embodiment, fewer wells 11 may be needed, because the nozzles may each release a spray or mist capable of covering a larger area. To diffuse the medicament 16 through the nozzles in a mist or spray, as opposed to, e.g., a drop, higher pressures may be required to force medicament 16 out of the nozzles. Pump 6 may increase the amount of fluid delivered to cavity 14 above membrane 7, or in direct-fill embodiments, pump 6 may deliver more or more highly pressurized medicament 16 to wells 11. In some embodiments, a gel or extra fluid layer may be located between medicament 16 and membrane 7 to allow membrane 7 to push onto the middle layer, which in turn may push medicament 16 out of the nozzle. This may allow the nozzle to continue spraying properly as the level of medicament 16 in wells 11 decreases. In such a configuration, the middle layer may be configured so as to not be delivered through the nozzle with medicament 16. In some embodiments, different wells 11 can have different types of nozzles, for instance, to allow different amounts and/or different rates of medicament 16 to flow from different wells 11. Further, wells 11 themselves do not need to be uniform. Such a non-uniform embodiment may be useful, for instance, when delivering multiple types of medicament 16 from the same patch 2.

In some embodiments, pump 6 may be configured to increase or decrease pressure in cavity 14 unevenly, so that some wells 11 empty, while others do not, or so that different wells 11 empty at different rates. In some embodiments, areas of membrane 7 may be less susceptible to deformation, so that some areas of membrane 7 require greater amounts of pressure before they will deform and apply pressure into certain wells 11. This may also cause certain wells 11 to empty differently than others.

The amount of fluid pumped into cavity 14 may thus determine the amount or speed of medicament delivered to the patient. Accordingly, the amount of medicament 16 delivered to a patient can be controlled and can be changed or adjusted over time. In some embodiments, the wearer of patch 2 may only hook patch 2 up to pump 6 when a dose of medicament is needed. In other embodiments, pump 6 may remain connected to patch 2 for an extended period of time, or permanently.

Figure 10A:
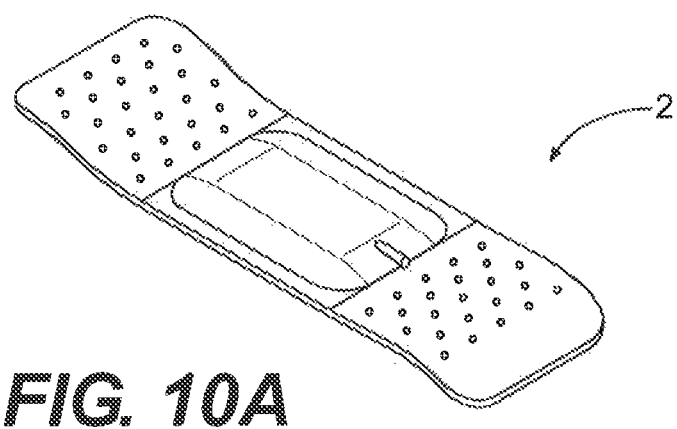
FIG. 10A depicts a perspective view of an exemplary direct medicament distribution device, in accordance with an embodiment of the present disclosure.
Figure 10B:
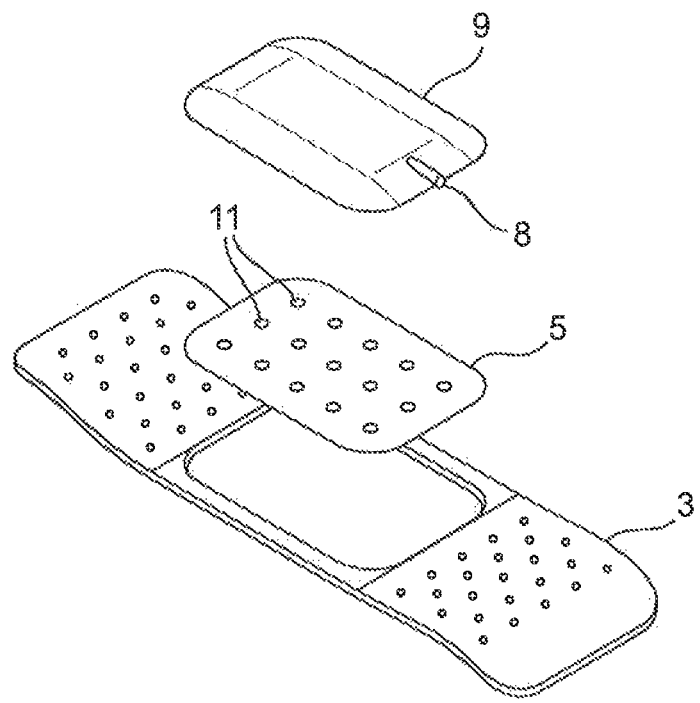
FIG. 10B depicts an exploded view of the exemplary direct medicament distribution device of FIG. 10A.

In some embodiments, wells 11 may not be pre-filled. In some embodiments, as shown in FIG. 10, pump 6 may directly deliver medicament 16 to patch 2 and wells 11. In this embodiment, patch 2 may not require fluid cavity 14 and/or membrane 7 to deliver medicament 16, allowing patch 2 to be more streamline. Instead, pump 6 may directly pump medicament 16 into wells 11. Medicament 16 may be delivered from pump 6 through connector 4, into wells 11, and out of wells 11 to the patient. In this embodiment, the medicament 16 may be stored in pump 6 and/or in an external storage container operably connected to pump 6. In such an embodiment, patch 2 may not include membrane 7. Pump 6 may include a removable cartridge for refilling pump 6 with medicament 16. In other embodiments, wells 11 may be pre-filled, and pump 6 may be configured to refill wells 11. In this embodiment, pump 6 may be configured to pump fluid into cavity 14, and/or may be configured to pump medicament 16 into wells 11, for example.

Figure 5:
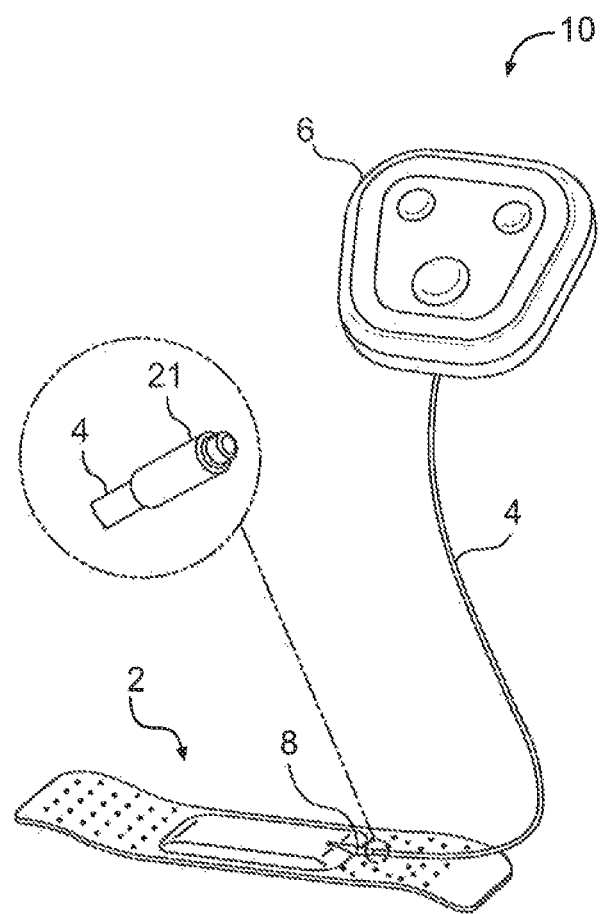
FIG. 5 depicts a perspective view of an exemplary medicament distribution device, in accordance with an embodiment of the present disclosure.
Figure 6:
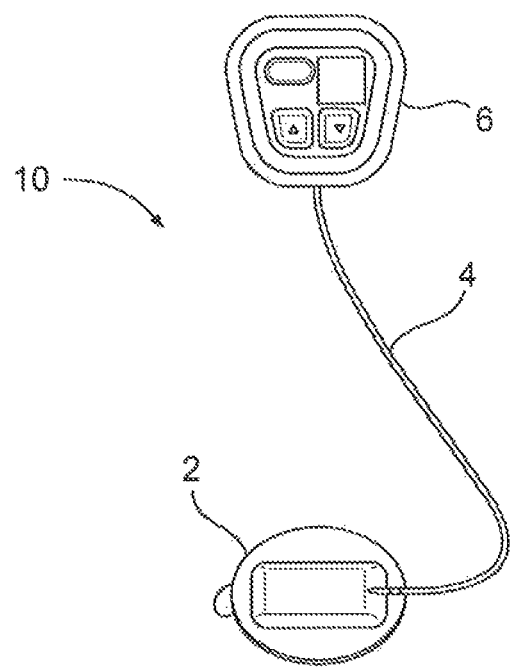
FIG. 6 depicts a perspective view of an exemplary medicament distribution device, in accordance with an embodiment of the present disclosure.
Figure 7A:
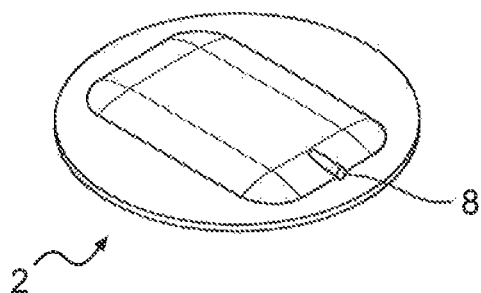
FIG. 7A depicts a perspective view of an exemplary device of FIG. 6.
Figure 7B:
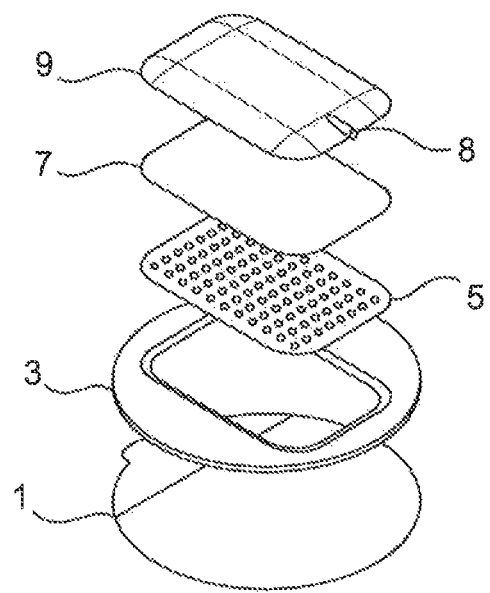
FIG. 7B depicts an exploded view of the exemplary device of FIG. 7A.

Pump 6 may be configured to deliver fluid, including medicament 16 in some embodiments, to patch 2 through connector 4, which may be a catheter or any other suitable connection device. Connector 4 may attach to port 8 or an opening in cover 9 of patch 2 and/or in cavity 14 and connect with a portion of pump 6. Connector 4 may twist, snap, friction fit, hook, or connect to patch 2 or pump 6 in any suitable manner. For instance, as shown in FIG. 5, connector 4 may include an elastomeric tubing 21 configured to twist in place onto port 8 on patch 2. Connector 4 may have one standard size, or different sizes may be available to correspond to sizes of patient, for example, children or adults. In another embodiment, connector 4 may be configured so as to have an adjustable size, e.g., an adjustable length. In such an embodiment, connector 4 may include a release mechanism, e.g. a button, lever, wind, etc., that allows the user to pull more slack out of pump 6, for instance, so as to lengthen connector 4, or alternatively, to allow extra slack to retract into pump 6 to shorten connector 4. Pump 6, connector 4, and/or patch 2 may include a mechanism to lock the length of connector 4 in place once a desired length has been achieved. In such embodiments, the length of the connection between pump 6 and patch 2 may be adjustable.

Figure 11A:
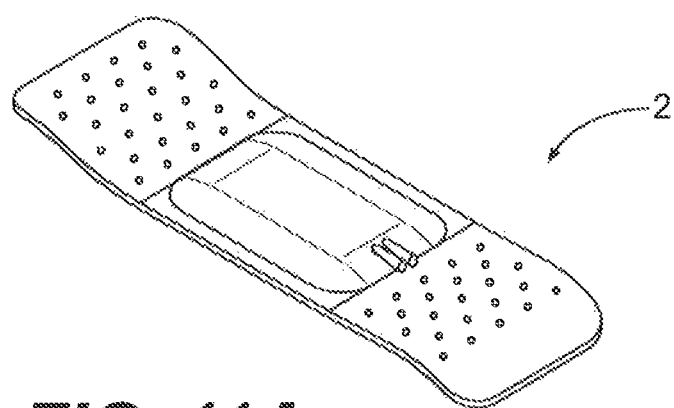
FIG. 11A depicts a perspective view of an exemplary medicament distribution device, in accordance with an embodiment of the present disclosure.
Figure 11B:
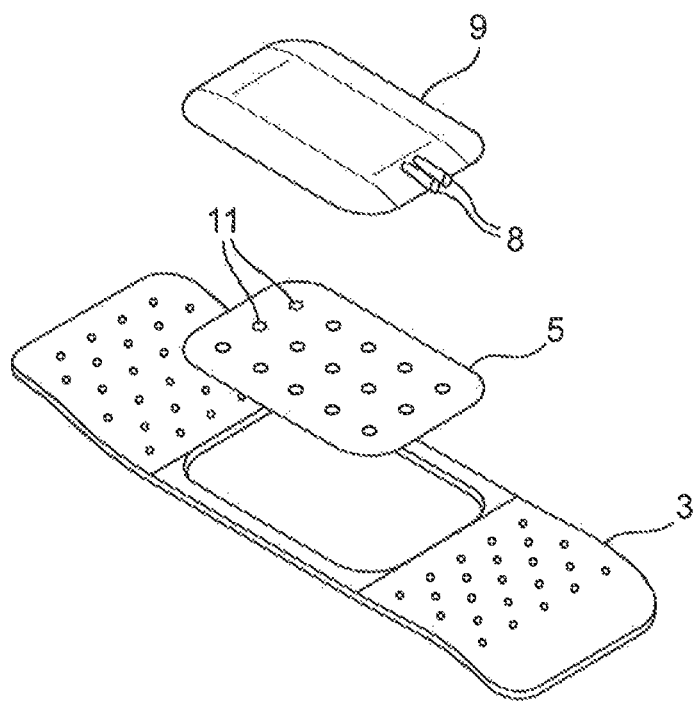
FIG. 11B depicts an exploded view of the exemplary medicament distribution device of FIG. 11A.

In some embodiments, medicament distribution system 10 may be configured to deliver more than one type of medicament 16 to a patient, as shown in FIG. 11. For instance, different wells 11 may be configured to contain, release, and/or deliver different medicaments 16. As discussed above, the pressure delivered to the different wells 11 or the resistance to deformation of membrane 7 that contacts different wells 11, for instance, may allow medicament delivery system 10 to deliver different amounts of medicaments 16, or to deliver amounts of medicaments 16 at different rates. This may also allow medicament delivery system 10 to separately control the delivery of two or more different types of medicaments 16. In such an embodiment, patch 2 may include more than one entry port 8 so as to allow patch 2 to connect to more than one connector 4, as shown in FIG. 11. In this manner, patch 2 may have more than one connection to pump 6. Having more than one connection to pump 6 may allow pump 6 to separately store and deliver more than one type of medicament 16 to patch 2. Medicaments 16 could be delivered from pump 6 to patch 2 at different times, different rates, different pressures, or in response to different input or feedback signals.

Each type of medicament 16 may be delivered from pump 6 to patch 2 in its own connector 4. In such an embodiment, connectors 4 may be configured to dispense medicament 16 into different regions of medicament array 5. One type of medicament 16 may be delivered to certain wells 11, while another type of medicament 16 may be delivered to other wells 11 located in a different region of medicament array 5, so as to keep the two medicaments 16 separate from one another. Further, having separate connectors 4 for each medicament 16 type may give pump 6 independent control over the timing and amount of each type of medicament 16 to be released.

In the multi-medicament embodiment, part of medicament array 5 may be pre-filled, while another part of medicament array 5 may be fed from pump 6. In this embodiment, some of medicament 16 for the unfilled portion may be stored in pump 6 or elsewhere and delivered during use. In other embodiments, each type of medicament 16 may be pre-filled or unfilled. In the multi-medicament embodiments, membrane 7 and/or medicament array 5 may have structures, such as barriers, seals, walls, or other mechanisms, configured to separate the sections of medicament arrays 5 and wells 11 for each type of medicament 16. In other embodiments, patch 2 may include a plurality of medicament arrays 5 and/or membranes 7 configured for use with different types of medicaments 16.

Pump 6 and/or patch 2 may further include any suitable gauge, display, or device for measuring and/or relaying the pressure in pump 6, cavity 14, or wells 11, and/or the amount of medicament 16 dispensed, and/or the amount of pressure-creating fluid released from pump 6. Pump 6 may be configured to precisely and accurately control the timing and amount of medicament 16 delivered to a patient. Pump 6 may be controlled by a processor, located either within pump 6 or external to pump 6. The processor may be, for instance, a programmable logic controller, or other suitable controller, that can be programmed by the patient or a physician to deliver medicament 16, e.g., at set intervals, as directed by a user or healthcare provider, in response to feedback, or as otherwise needed. Programming may be accomplished using a USB cable, one or more buttons, a touch screen, or any other suitable actuation and/or input mechanisms on pump 6 or the external controller. In one embodiment, programming can be done wirelessly, for example through a mobile device, such as a smart phone or computer. For instance, a healthcare provider may be able to control medicament delivery remotely through a wireless connection. This may allow a healthcare provider to upload new dosing profiles during, or even between visits, while allowing the patient the ability to make any necessary adjustments while outside of professional care.

In addition, pump 6 may be operably coupled to a controller with a memory or a processor configured to store and/or process information regarding drug delivery events and/or patient parameters. Information may be logged and time stamped, allowing the patient or physician to better track and/or analyze drug delivery history and/or patient response, and to ultimately improve patient care. This information may be relayed through a wireless connection to a healthcare provider so that the provider may track dosing and/or patient data, such as patient response to the medicament, in real time or from a stored history, from a remote location. In addition, the provider may be able to adjust the dosages and/or medicament type remotely. In some embodiments, the controller may automatically control dosing, e.g., through a timer, or through the use of feedback, or a user or healthcare provider may be able to manually control the timing and dosage. In other embodiments, both may be possible, for instance, pump 6 may have automatic and manual modes, or pump 6 may be automated, but may also have a manual override option.

Further, pump 6 and/or an external controller may provide information and/or feedback and/or readings to a user or provider, through, e.g., visual signals on a display or through tactile or auditory signals. Patch 2 and/or the pump 6 may include a display screen, e.g., a graphical display screen. In one embodiment, for instance, patch 2 or an indicator on pump 6 may change color, blink, or display an image when medicament 16 is running low and a medicament array 5 needs to be switched and/or refilled, or a medicament cartridge in pump 6 needs to be switched and/or refilled. Other indicators may include auditory signals, such as beeps, for instance.

When it is time for the controller to deliver a quantity of medicament, the microcontroller may send an actuation signal to pump 6. This may create a positive pressure at the pump outlet through the use of actuation mechanisms. Pump 6 may include a magnet and/or an electromagnetic coil and/or medicament delivery system 10 may be configured to function with several pumps 6. For instance, exemplary pumps and actuation mechanisms are described in U.S. patent application Ser. No. 13/448,013, filed Apr. 16, 2012, and Ser. No. 13/470,140, filed May 5, 2012, of which the entirety of each is incorporated herein by reference. This pressure may be in fluid communication with connector 4 that transmits the pressure signal to patch 2. The pressure may cause a deflection in patch membrane 7, which may impart a force on medicament array 5, as described above. The force on medicament array 5 may cause wells 11 to open and deliver a quantity of medicament 16, which may be proportional to the pressure signal delivered by the controller.

Figure 8A:
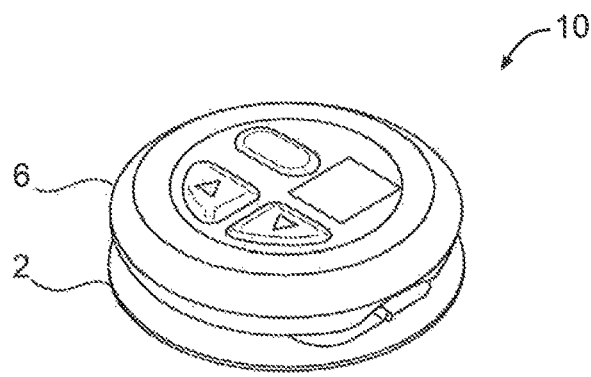
FIG. 8A depicts a perspective view of an exemplary medicament distribution device, in accordance with an embodiment of the present disclosure.
Figure 8B:
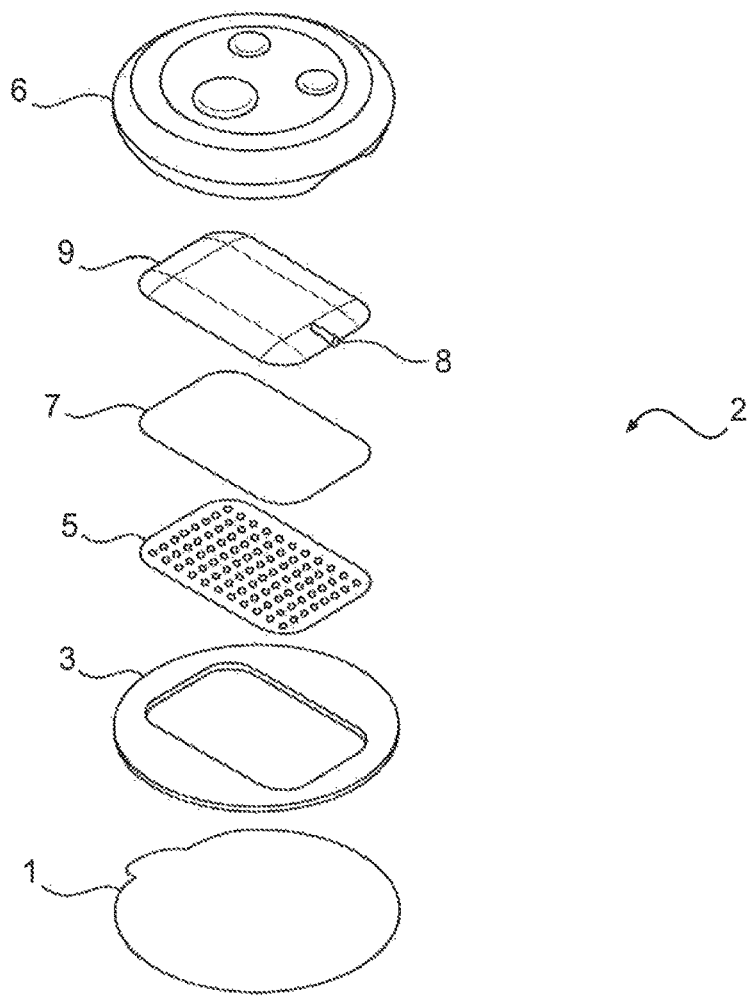
FIG. 8B depicts an exploded view of the exemplary medicament distribution device of FIG. 8A.
Figure 9A:
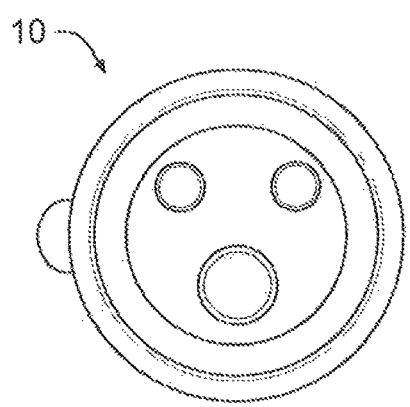
FIG. 9A depicts a top view of an exemplary medicament distribution device, in accordance with an embodiment of the present disclosure.
Figure 9B:
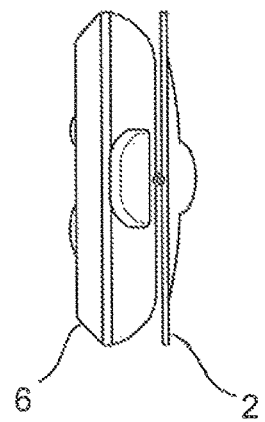
FIG. 9B depicts a side view of the exemplary medicament distribution device of FIG. 9A.
Figure 9C:
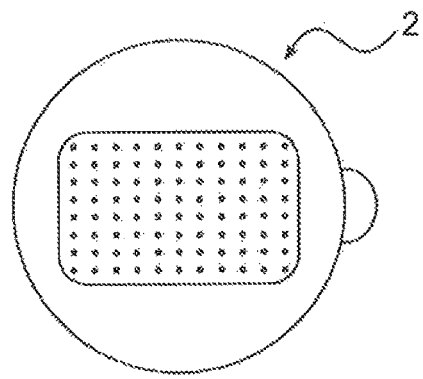
FIG. 9C depicts a bottom view of the exemplary medicament distribution device of FIG. 9A.
Figure 9D:
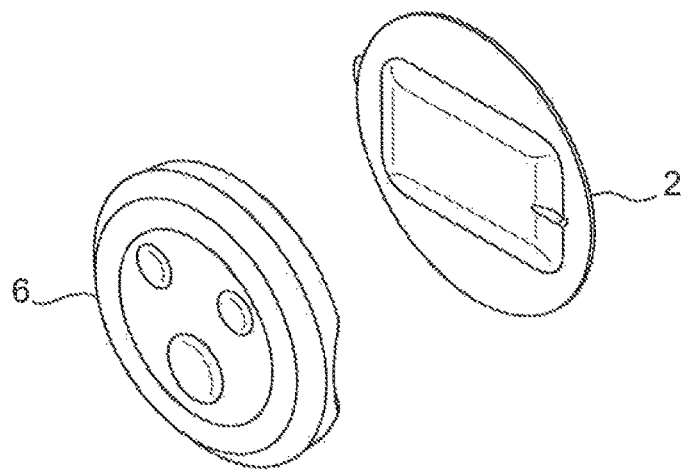
FIG. 9D depicts an exploded view of the exemplary medicament distribution device of FIG. 9A.

In some embodiments, a small, lightweight pump 6 may be affixed to the user using a stick-to-skin adhesive backing, or any other suitable connection device, as discussed above, and can be attached to any location relative to patch 2. In one embodiment, pump 6 may be located near the patch, for instance, adjacent to patch 2. In some embodiments, patch 2 and pump 6 may be integrated. In an integrated embodiment, patch 2 and pump 6 can be directly coupled to one another, as shown in FIGS. 8 and 9. Pump 6 may integrate directly with patch 2, thereby reducing the number of adhesive sites, points of connection, or the number of different components the patient may need to carry or keep track of. For example, patch 2 and pump 6 may have inlets and outlets that directly fluidly couple patch 2 and pump 6, eliminating the need for connector 4. For instance, pump 6 may be attached to an upper portion of patch cover 9. Patch 2 and pump 6 may be connected, e.g., via a strap, Velcro®, magnets, clips, elastic, or pump 6 and patch 2 may be shaped, sized, or configured to snap, slide, twist, or otherwise lock into one another. In this embodiment, pump 6 and patch 2 may be permanently coupled or may be removably coupled to one another. If permanently coupled, medicament delivery system 10 may be disposable. In the removable embodiment, medicament delivery system 10 may be disposable, or pump 6 may be reusable, or pump 6 and patch 2 may be reusable. In some embodiments, pump 6 and patch 2 may disconnect so as to allow the wearer to replace patch 2, for instance, if medicament 16 in patch 2 has been depleted. In one embodiment, patch 2 may be removable and may be sterilized and reapplied for multiple uses. Locating pump 6 adjacent to or near patch 2 may be useful for situations in which medicament 16 must be delivered to a larger area of a patient.

In some embodiments, medicament delivery system 10 may be configured to deliver medicament 16 topically to the skin of a patient. Patch 2 can be worn in any location on a patient, for instance, on an arm, a leg, a foot, a hand, the back, the abdomen, or any other anatomical region. In other embodiments, medicament 16 may be configured for delivery just below the skin, for instance, for delivery between the epidermis and the dermis, or for subcutaneous delivery. In these embodiments, patch 2 may be configured to scratch the skin prior to delivery, for instance, with a rough surface or with one or more needles. In another embodiment, patch 2 may include a number of needles and/or catheters configured to penetrate into the wearer while patch 2 is attached to the wearer. In this embodiment, medicament 16 may be delivered out of wells 11 and into one or more needles or catheters to a region below the skin. In another embodiment, needles may temporarily penetrate the skin and may then retract. In such an embodiment, medicament 16 may be delivered either while the needles and/or catheters are penetrating into the wearer, or before and/or after penetrating the wearer. For example, medicament 16 may be delivered through a needle and/or catheter while penetrating the wearer or delivered topically once the skin has been penetrated. In still other embodiments, patch 2 may be configured to deliver medicament 16 both topically and subcutaneously.

In another embodiment, medicament delivery system 10 may include a feedback control and/or monitoring system. Medicament delivery system 10 may include one or more sensors, for instance, an electrode, thermometer, or any other suitable sensor, configured to continuously monitor one or more parameters of a patient, for instance, nerve conduction velocity (NCV). An NCV test is an electrical test that is used to detect abnormal nerve conditions. This type of test may determine how severe a nerve condition is and may be used in conjunction with device 10 of the present disclosure to determine how a nerve responds to treatment, or to adjust the dosage level and/or type and/or timing of medicament 16 administered, for instance.

Figure 12:
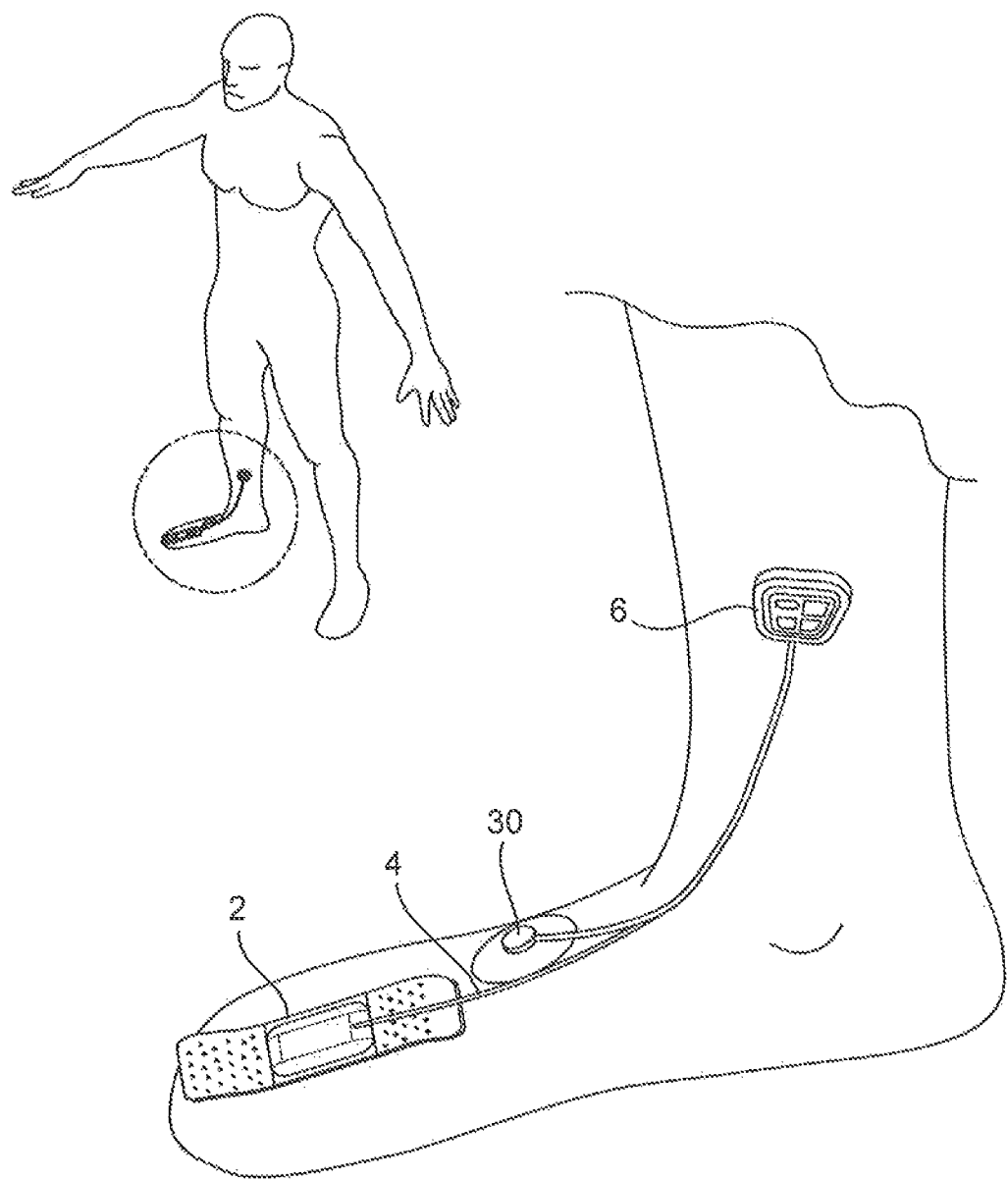
FIG. 12 depicts a perspective view of an exemplary medicament distribution device, in accordance with an embodiment of the present disclosure.

Turning to FIG. 12, the monitoring and/or feedback system may include one or more electrodes 30, e.g., two or three electrodes, to detect the effectiveness of medicament dosing and/or patient response, for instance, receptiveness of pain management or healing. One electrode 30 may be located near or may be integrated with pump 6 on the surface of the patient's skin. Another electrode 30 (not shown) may be located some distance away from first electrode 30, for instance, near or integrated into patch 2. Electrical signals may be communicated via specific nerves in the body, e.g., in the arms, legs, back, or abdomen, starting from one electrode (the stimulating electrode) in contact with the skin to another electrode (the recording electrode). The second electrode may be placed downstream of the first electrode and may be used to detect the electrical impulse. One or more nerves may be stimulated with an electrical current impulse discharged from the stimulating electrode. The electrical activity may be detected by the recording electrode. The electrodes may measure the nerve response to the medicament by monitoring how fast (latency) electrical impulses are travelling, because a damaged nerve may transmit electrical signals slower and/or weaker than a healthy nerve. The time it takes for the electrical signals to travel between electrodes and the distance between them may be used to calculate the speed of the nerve signal. The size of the velocity response—called the amplitude—may also measured.

By including a small NCV testing system within medicament delivery system 10, the system may be able to continuously monitor the health of the patient's nerves. This may provide information to allow device 10 and healthcare providers to evaluate the effectiveness of treatment, while also allowing medicament delivery system 10 to adjust dosing levels based on the feedback response from the patient's nerves. For instance, medicament delivery system 10 may be a 'smart' delivery system and may include algorithms and programming within pump 6 or a separate controller that are capable of receiving input from electrodes 30 and using this feedback to adjust the dosage, rate, and/or type of medicament 16 delivered. This may optimize patient dosing and reduce the administration of too much or too little medicament 16, minimizing any potential side effects. This may result in a delivery system capable of adapting to the needs of the patient to ensure optimal treatment and/or diagnosis. In other embodiments, EMG tests or other tests for measuring and assessing patient parameters, such as blood glucose levels, etc., may be integrated into medicament delivery system 10 so as to provide feedback and monitoring to the system.

Embodiments of medicament delivery system 10 and pump control unit, with the help of a physician, can be programmed to treat the symptoms of PN and monitor patient response as a function of dosage and nerve conductivity response. This feedback and control delivery system offers physicians and healthcare providers the ability to effectively manage and treat PN. By creating a feedback mechanism, the device can assess how the patient's nerves are responding to the treatment and can adjust the dosing profile accordingly. Furthermore, patients can then assess pain, numbness, burning, or tingling, for example, that may be relieved, and patients can also make adjustments on their own. An intelligent, controlled topical drug delivery device can better indicate how well a nerve is functioning, and therefore help to determine how much medicament should be delivered onto or below the skin. The medicament delivery system may also be capable of delivering more than one medicament, presenting an opportunity to deliver additional drugs, such as, e.g., a growth factor, that may help to heal some of the nerve damage caused by PN.

When combining the NCV testing system and the electrodes for monitoring receptiveness of pain management or healing, the disclosed system may become an integrated pain management system that can be used on different parts of the body to treat different pathologies, for instance, skin pathologies such as PN.

Further, in some embodiments, it is contemplated that medicament delivery system 10 may include additional optional features. Such features may include, but are not limited to, circuitry relating to fitness and/or a user's lifestyle. For example, the system may include an integrated pedometer, a global positioning system (GPS), a music player, and so forth. This may be ideal for, for instance, diabetic patients who have been prescribed exercise as part of their health regimen. In other embodiments, the system may be configured to integrate with a device, such as a watch, computer, or a smart phone, e.g., through an application or program, to allow a user or a healthcare provider to control the system and/or monitor drug delivery, patient parameters, or patient response, from the external device.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the claims are not to be considered as limited by the foregoing description.

What is claimed is:

1. A medical device for releasing a medicament, comprising:
    a multi-layer patch, including:
        a base layer configured to secure the patch to a body of a user;
        a medicament array located adjacent the base layer, wherein the medicament array includes a plurality of wells each configured to contain and release a quantity of medicament from the medicament array to the body of the user; a bottom surface of each of the plurality of wells being configured to allow the quantity of medicament contained in each well to pass from the well to the body of the user in response to an increase in pressure against the well, and wherein the medicament array is configured to be elevated off of the body of the user when the patch is secured to the body of the user;
        a cover layer located on a side of the medicament array opposite the base layer;
    a pump operably coupled to the patch and configured to deliver a quantity of fluid to the patch;
    a controller operably coupled to the pump; and
    one or more sensors configured to measure one or more body parameters, wherein at least one body parameter is at least partially indicative of an effectiveness of the quantity of medicament, wherein the sensors are configured to relay information about the one or more body parameters to the controller, wherein at least one sensor is located on or proximate to the multi-layer patch, wherein at least one sensor comprises one or more electrodes and at least one body parameter comprises nerve conduction velocity, and wherein one or both the controller and pump comprise programming configured to receive input feedback from the one or more sensors, wherein the input feedback is used to adjust one or more dosage and delivery rate.

2. The medical device of claim 1, wherein the multi-layer patch further includes a membrane located between the cover layer and the medicament array, and wherein the cover layer and the membrane define a cavity configured to hold the quantity of fluid, and wherein the membrane is configured to deform into the plurality of wells in response to an increased volume of fluid in the cavity.

3. The medical device of claim 1, wherein the cover layer further includes at least one port connecting an inner region of the cover layer with an outer region of the cover layer, wherein the port is configured to receive a catheter to operably connect the multi-layer patch to the pump.

4. The medical device of claim 3, wherein the cover layer includes two ports and the medical device is configured to release more than one type of medicament.

5. The medical device of claim 1, wherein the pump is located adjacent to the multi-layer patch.

6. The medical device of claim 1, wherein the fluid released from the pump to the multi-layer patch includes one or more medicaments.

7. The medical device of claim 6, wherein the pump includes a cartridge configured to store the one or more medicaments.

8. The medical device of claim 1, further including a removable seal adjacent the base layer, wherein removal of the seal exposes an adhesive for securing the multi-layer patch to the body of the user.

9. The medical device of claim 6, wherein the input feedback is further used to adjust the type of medicament delivered.

10. A medical device for releasing a medicament, comprising:
    a patch including a medicament array having a plurality of wells each configured to contain and release a quantity of medicament from a storage region of the wells to a body of a user, wherein the medicament array is configured to be elevated off of the body of the user when the patch is secured to the body of the user;

a pump operably coupled to the patch and configured to deliver a quantity of fluid from the pump to a region above the storage region of the wells, and wherein a bottom surface of each of the plurality of wells is configured to allow the quantity of medicament contained in each well to pass from the well to the body of the user in response to an increase in pressure against the well caused by an increase in the quantity of fluid delivered from the pump;

a controller operably coupled to the pump; and one or more sensors configured to measure one or more body parameters, wherein at least one body parameter is at least partially indicative of an effectiveness of the quantity of medicament, wherein the sensors are configured to relay information about the one or more body parameters to the controller, and wherein at least one sensor is located on or proximate to the patch, wherein at least one sensor comprises one or more electrodes and at least one body parameter comprises nerve conduction velocity, and wherein the one or more sensors comprises at least two electrodes, and the one or more body parameters includes an electrical activity of one or more nerves or muscles wherein the controller is configured to adjust the quantity, timing, or type of fluid delivered from the pump to the patch based on the information received from the one or more sensors.

11. The medical device of claim 10, wherein the patch further includes a membrane adjacent the medicament array, wherein the membrane is configured to deform into the plurality of wells in response to the increase in the quantity of fluid delivered from the pump.

12. The medical device of claim 10, wherein the one or more sensors are configured to continuously monitor the one or more body parameters.

13. A medical device for releasing a medicament, comprising:

a patch including a medicament array having a plurality of wells each configured to contain and release a quantity of medicament from the medicament array to a body of a user; each of the wells having an opening located in a bottom surface that is configured to release the quantity of medicament contained in each well from the well to the body of the user in response to an increase in pressure against the well, and wherein the medicament array is configured to be elevated off of the body of the user when the patch is secured to the body of the user;

a membrane located adjacent the plurality of wells and configured to deform into the plurality of wells;

a mechanism configured to secure the patch to the body of the user;

a pump configured to deliver a quantity of fluid to the patch, wherein the delivery of fluid increases an amount of pressure on the membrane, causing the membrane to deform into the plurality of wells and causing the wells to release the quantity of medicament through the openings and to the body of the user;

wherein the medical device includes a controller configured to control the delivery of fluid from the pump to the patch; and one or more sensors configured to measure one or more body parameters, wherein at least one body parameter is at least partially indicative of an effectiveness of the quantity of medicament, wherein the sensors are configured to relay information about the one or more body parameters to the controller, and wherein at least one sensor is located on or proximate to the patch, wherein at least one sensor comprises one or more electrodes and at least one body parameter comprises nerve conduction velocity, and wherein the one or more sensors comprises at least two electrodes, and the one or more body parameters includes an electrical activity of one or more nerves or muscles, wherein the controller is configured to adjust the quantity, timing, or type of fluid delivered from the pump to the patch based on the information received from the one or more sensors.

14. The medical device of claim 13, wherein the controller is a programmable logic controller.

15. The medical device of claim 13, wherein the controller is wirelessly coupled to an input device and configured to receive input from a remote user.

16. The medical device of claim 13, wherein the medicament array is configured to contain and release a plurality of medicaments.

17. The medical device of claim 16, wherein the medicament array is configured to release a first medicament of the plurality of medicaments at a first rate and to release a second medicament of the plurality of medicaments at a second rate, wherein the second rate is different from the first rate.

* * * * *